US008642561B2

(12) United States Patent
Jiang et al.

(10) Patent No.: US 8,642,561 B2
(45) Date of Patent: Feb. 4, 2014

(54) PEPTIDES WHOSE UPTAKE BY CELLS IS CONTROLLABLE

(75) Inventors: Tao Jiang, San Diego, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/314,134

(22) Filed: Dec. 7, 2011

(65) Prior Publication Data
US 2012/0251445 A1    Oct. 4, 2012

Related U.S. Application Data

(63) Continuation of application No. 12/244,602, filed on Oct. 2, 2008, now Pat. No. 8,110,554, which is a continuation of application No. 10/699,562, filed on Oct. 31, 2003, now Pat. No. 7,431,915.

(51) Int. Cl.
| | |
|---|---|
| *A61K 38/06* | (2006.01) |
| *A61K 38/16* | (2006.01) |
| *A61K 38/10* | (2006.01) |
| *G01N 33/533* | (2006.01) |
| *C07H 19/04* | (2006.01) |
| *G03F 7/00* | (2006.01) |

(52) U.S. Cl.
USPC ....... 514/21.6; 514/21.3; 514/21.4; 514/21.8; 530/328; 530/327; 530/326; 430/270.19; 436/546; 536/26.6

(58) Field of Classification Search
None
See application file for complete search history.

(56) References Cited

U.S. PATENT DOCUMENTS

| | | | |
|---|---|---|---|
| 4,466,919 A | 8/1984 | Weingarten | |
| 4,507,389 A | 3/1985 | Weingarten | |
| 5,674,980 A | 10/1997 | Frankel et al. | |
| 5,747,641 A | 5/1998 | Frankel et al. | |
| 5,910,300 A | 6/1999 | Tournier et al. | |
| 6,306,993 B1 * | 10/2001 | Rothbard et al. | 526/304 |
| 6,348,185 B1 | 2/2002 | Piwnica-Worms | |
| 7,431,915 B2 | 10/2008 | Jiang et al. | |
| 7,985,401 B2 | 7/2011 | Jiang et al. | |
| 2001/0021763 A1 | 9/2001 | Harris | |
| 2002/0009786 A1 * | 1/2002 | Tang et al. | 435/183 |
| 2003/0176335 A1 | 9/2003 | Zhang et al. | |
| 2004/0009122 A1 | 1/2004 | Klaveness et al. | |
| 2004/0241096 A1 | 12/2004 | Bogdanov et al. | |
| 2005/0107583 A1 | 5/2005 | Jiang et al. | |
| 2006/0041105 A1 | 2/2006 | Jiang et al. | |
| 2007/0041904 A1 | 2/2007 | Jiang et al. | |
| 2009/0004118 A1 | 1/2009 | Nie et al. | |

FOREIGN PATENT DOCUMENTS

| | | | |
|---|---|---|---|
| WO | WO-01/75067 | * | 10/2001 |
| WO | WO 01/75067 A2 | | 10/2001 |
| WO | 2005/042034 A1 | | 5/2005 |
| WO | WO 2005/042034 A1 | | 5/2005 |

OTHER PUBLICATIONS

Bartles, J.R. et al., "Identification and charactzerization of espin, an actin-binding protein localized to the F-actin0rich junctionla plaques of Sertoli cell ectoplasmic specializations," *Journal of Cell Science*, 1996, vol. 109, No. 6, pp. 1229-1239.
Bhorade, R. et al., "Macrocyclic Chelators with Paramagnetic Cations Are Internalized into Mammalian Cells via a HIV-Tat Derived Membrane Translocation Peptide," *Bioconjugate Chemistry*, May 1, 2000, vol. 11, No. 3, pp. 301-305.
Golub et al., *Science*, Oct. 15, 1999, pp. 531-537.
Jiang, T. et al., "Tumor imaging by means of proteolytic activation of cell-penetrating peptides," *PNAS*, Dec. 21, 2004, pp. 17867-17872, vol. 101, No. 51.
Rothbard, J. B. et al., "Conjugation of arginine oligomers to cyclosporin A facilitates topical delivery and inhibition of inflammation," *Nature Medicine*, Nov. 2000, vol. 6, No. 11, pp. 1253-1257.
Rothbard, J.B. et al., "Arginine-Rich Molecular Transporters for Drug Delivery: Role of Backbone Spacing in Cellular Uptake," *J. Med. Chem.*, 2002, vol. 45, pp. 3612-3618.
Tung, C-H. et al., "Arginine containing peptides as delivery vectors," *Advanced Drug Delivery Reviews*, 2003, vol. 55, pp. 281-294.
Ullrich, K.J. et al., "Controluminal para-aminohippurate (PAH) transport in the proximal tubule of the rat kidney," *Pflügers Arch.*, 1989, vol. 415, pp. 342-350.
Wang, Y. et al., "Visualizing the mechanical activation of Src," *Nature*, Apr. 21, 2005, pp. 1040-1045, vol. 434.
Wender, P.A. et al., "The design, synthesis, and evaluation of molecules that enable or enhance cellular uptake: Peptoid molcular transporters," *PNAS*, Nov. 21, 2000, vol. 97, No. 24, pp. 13003-13008.

* cited by examiner

*Primary Examiner* — Satyanarayana R Gudibande
(74) *Attorney, Agent, or Firm* — Morgan, Lewis & Bockius LLP

(57) ABSTRACT

A generic structure for the peptides of the present invention includes A-X-B-C, where C is a cargo moiety, the B portion includes basic amino acids, X is a cleavable linker sequence, and the A portion includes acidic amino acids. The intact structure is not significantly taken up by cells; however, upon extracellular cleavage of X, the B-C portion is taken up, delivering the cargo to targeted cells. Cargo may be, for example, a contrast agent for diagnostic imaging, a chemotherapeutic drug, or a radiation-sensitizer for therapy. Cleavage of X allows separation of A from B, unmasking the normal ability of the basic amino acids in B to drag cargo C into cells near the cleavage event. X is cleaved extracellularly, preferably under physiological conditions. D-amino acids are preferred for the A and B portions, to minimize immunogenicity and nonspecific cleavage by background peptidases or proteases.

11 Claims, 39 Drawing Sheets

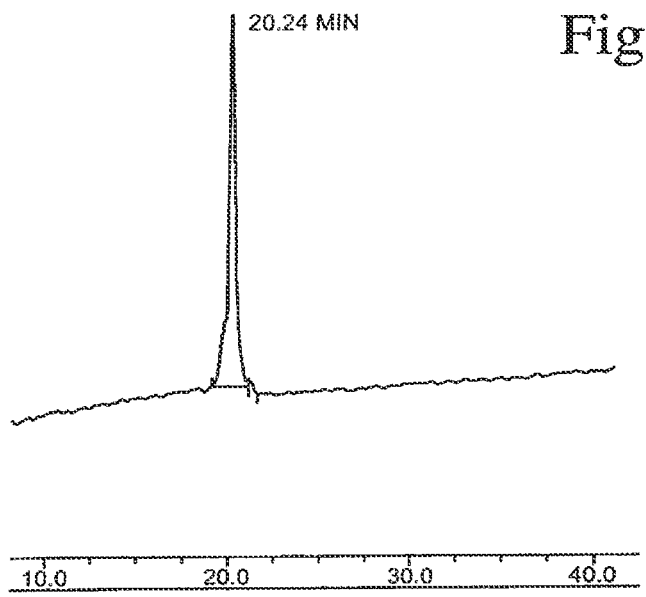
Figure 6A
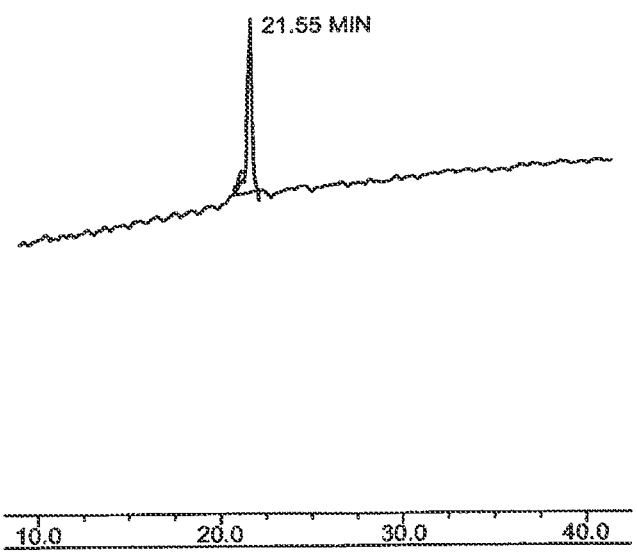
AFTER ENTEROKINASE CLEAVAGE: Figure 6B

```
                      SEQUENCE LISTING

<160> NUMBER OF SEQ ID NOS: 56

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:linker X
      cleavable by matrix metalloproteinase-2 (MMP-2)
      and meprin

<400> SEQUENCE: 1

Pro Leu Gly Leu Ala Gly
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:cleavable
      linker

<400> SEQUENCE: 2

Glu Asp Asp Asp Asp Lys Ala
  1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:peptide
      designed to be substrate for enterokinase
<220> FEATURE:
<221> NAME/KEY: MOD_RES
<222> LOCATION: (8)
<223> OTHER INFORMATION: Xaa = aminohexanoic acid (aminocaproic acid)
<220> FEATURE:
<221> NAME/KEY: MOD_RES
<222> LOCATION: (18)
<223> OTHER INFORMATION: Xaa = aminohexanoic acid (aminocaproic acid)
<220> FEATURE:
<221> NAME/KEY: MOD_RES
<222> LOCATION: (19)
<223> OTHER INFORMATION: Xaa = cysteinamide modified by fluorescein (Fl)

<400> SEQUENCE: 3

Glu Asp Asp Asp Asp Lys Ala Xaa Arg Arg Arg Arg Arg Arg Arg
  1               5                  10                  15

Arg Xaa Xaa

<210> SEQ ID NO 4

<400> SEQUENCE: 4

000
```

```
<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:peptide 5-
      47, oligoglutamates veto oligoarginine-mediated cellular uptake
<220> FEATURE:
<221> NAME/KEY: MOD_RES
<222> LOCATION: (1)
<223> OTHER INFORMATION: Xaa = aminohexanoic acid (aminocaproic acid)
      modified by fluorescein (Fl)
<220> FEATURE:
<221> NAME/KEY: MOD_RES
<222> LOCATION: (12)
<223> OTHER INFORMATION: Xaa = aminohexanoic acid (aminocaproic acid)
<220> FEATURE:
<221> NAME/KEY: MOD_RES
<222> LOCATION: (22)
<223> OTHER INFORMATION: Xaa = cysteinamide

<400> SEQUENCE: 5

Xaa Cys Arg Arg Arg Arg Arg Arg Arg Arg Xaa Glu Glu Glu Glu
  1               5                  10                  15

Glu Glu Glu Glu Glu Xaa
                20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:peptide 6-
      10, oligoglutamates veto oligoarginine-mediated cellular uptake
<220> FEATURE:
<221> NAME/KEY: MOD_RES
<222> LOCATION: (1)
<223> OTHER INFORMATION: Xaa = aminohexanoic acid (aminocaproic acid)
      modified by fluorescein (Fl)
<220> FEATURE:
<221> NAME/KEY: MOD_RES
<222> LOCATION: (7)
<223> OTHER INFORMATION: Xaa = aminohexanoic acid (aminocaproic acid)
<220> FEATURE:
<221> NAME/KEY: MOD_RES
<222> LOCATION: (17)
<223> OTHER INFORMATION: Xaa = cysteinamide

<400> SEQUENCE: 6

Xaa Cys Glu Glu Glu Glu Xaa Arg Arg Arg Arg Arg Arg Arg Arg
  1               5                  10                  15

Xaa

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence:peptide 6-
      14, enterokinase substrate cleavage-dependent cellular uptake
<220> FEATURE:
<221> NAME/KEY: MOD_RES
<222> LOCATION: (12)
<223> OTHER INFORMATION: Xaa = aminohexanoic acid (aminocaproic acid)
<220> FEATURE:
<221> NAME/KEY: MOD_RES
<222> LOCATION: (22)
<223> OTHER INFORMATION: Xaa = aminohexanoic acid (aminocaproic acid)
<220> FEATURE:
<221> NAME/KEY: MOD_RES
<222> LOCATION: (23)
<223> OTHER INFORMATION: Xaa = cysteinamide modified by fluorescein (Fl)

<400> SEQUENCE: 7
```

```
Glu Glu Glu Glu Glu Asp Asp Asp Asp Lys Ala Xaa Arg Arg Arg Arg
1               5                   10                  15

Arg Arg Arg Arg Arg Xaa Xaa
                20
```

```
<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence:peptide 6-
      16, enterokinase substrate cleavage-dependent cellular uptake
<220> FEATURE:
<221> NAME/KEY: MOD_RES
<222> LOCATION: (8)
<223> OTHER INFORMATION: Xaa = aminohexanoic acid (aminocaproic acid)
<220> FEATURE:
<221> NAME/KEY: MOD_RES
<222> LOCATION: (18)
<223> OTHER INFORMATION: Xaa = aminohexanoic acid (aminocaproic acid)
<220> FEATURE:
<221> NAME/KEY: MOD_RES
<222> LOCATION: (19)
<223> OTHER INFORMATION: Xaa = cysteinamide modified by fluorescein (Fl)

<400> SEQUENCE: 8
```

```
Glu Asp Asp Asp Asp Lys Ala Xaa Arg Arg Arg Arg Arg Arg Arg Arg
1               5                   10                  15

Arg Xaa Xaa
```

```
<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence:peptide 6-
      27, enterokinase substrate cleavage-dependent cellular uptake
<220> FEATURE:
<221> NAME/KEY: MOD_RES
<222> LOCATION: (21)
<223> OTHER INFORMATION: Xaa = aminohexanoic acid (aminocaproic acid)
<220> FEATURE:
<221> NAME/KEY: MOD_RES
<222> LOCATION: (22)
<223> OTHER INFORMATION: Xaa = cysteinamide modified by fluorescein (Fl)

<400> SEQUENCE: 9
```

```
Glu Glu Glu Glu Glu Asp Asp Asp Asp Lys Ala Arg Arg Arg Arg
1               5                   10                  15

Arg Arg Arg Arg Xaa Xaa
                20
```

```
<210> SEQ ID NO 10

<400> SEQUENCE: 10

000
```

```
<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence:peptide 7-2,
      enterokinase substrate cleavage-dependent cellular
      uptake
<220> FEATURE:
<221> NAME/KEY: MOD_RES
<222> LOCATION: (18)
<223> OTHER INFORMATION: Xaa = aminohexanoic acid (aminocaproic acid)
```

```
<220> FEATURE:
<221> NAME/KEY: MOD_RES
<222> LOCATION: (19)
<223> OTHER INFORMATION: Xaa = cysteinamide modified by fluorescein (Fl)

<400> SEQUENCE: 11

Asp Asp Asp Asp Asp Asp Lys Ala Arg Arg Arg Arg Arg Arg Arg
 1               5                  10                  15

Arg Xaa Xaa

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence:peptide 7-4,
      enterokinase substrate cleavage-dependent cellular uptake
<220> FEATURE:
<221> NAME/KEY: MOD_RES
<222> LOCATION: (10)
<223> OTHER INFORMATION: Xaa = aminohexanoic acid (aminocaproic acid)
<220> FEATURE:
<221> NAME/KEY: MOD_RES
<222> LOCATION: (13)
<223> OTHER INFORMATION: Xaa = aminohexanoic acid (aminocaproic acid)
<220> FEATURE:
<221> NAME/KEY: MOD_RES
<222> LOCATION: (16)
<223> OTHER INFORMATION: Xaa = aminohexanoic acid (aminocaproic acid)
<220> FEATURE:
<221> NAME/KEY: MOD_RES
<222> LOCATION: (19)
<223> OTHER INFORMATION: Xaa = aminohexanoic acid (aminocaproic acid)
<220> FEATURE:
<221> NAME/KEY: MOD_RES
<222> LOCATION: (22)
<223> OTHER INFORMATION: Xaa = aminohexanoic acid (aminocaproic acid)
<220> FEATURE:
<221> NAME/KEY: MOD_RES
<222> LOCATION: (23)
<223> OTHER INFORMATION: Xaa = cysteinamide modified by fluorescein (Fl)

<400> SEQUENCE: 12

Glu Glu Asp Asp Asp Asp Lys Ala Arg Xaa Arg Arg Xaa Arg Xaa
 1               5                  10                  15

Arg Arg Xaa Arg Arg Xaa Xaa
            20

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000
```

```
<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:membrane-
      translocating sequence (MTS)
<220> FEATURE:
<221> NAME/KEY: MOD_RES
<222> LOCATION: (4)
<223> OTHER INFORMATION: Xaa = aminohexanoic acid (aminocaproic acid)
<220> FEATURE:
<221> NAME/KEY: MOD_RES
<222> LOCATION: (10)
<223> OTHER INFORMATION: Xaa = aminohexanoic acid (aminocaproic acid)
<220> FEATURE:
<221> NAME/KEY: MOD_RES
<222> LOCATION: (11)
<223> OTHER INFORMATION: Xaa = cysteinamide modified by fluorescein (Fl)

<400> SEQUENCE: 17

Glu Asp Ala Xaa Arg Arg Arg Arg Arg Xaa Xaa
 1               5                  10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:membrane-
      translocating sequence (MTS)
<220> FEATURE:
<221> NAME/KEY: MOD_RES
<222> LOCATION: (8)
<223> OTHER INFORMATION: Xaa = aminohexanoic acid (aminocaproic acid)
<220> FEATURE:
<221> NAME/KEY: MOD_RES
<222> LOCATION: (15)
<223> OTHER INFORMATION: Xaa = aminohexanoic acid (aminocaproic acid)
<220> FEATURE:
<221> NAME/KEY: MOD_RES
<222> LOCATION: (16)
<223> OTHER INFORMATION: Xaa = cysteinamide modified by doxorubicin
      (DOX)

<400> SEQUENCE: 18

Glu Asp Asp Asp Asp Lys Ala Xaa Arg Arg Arg Arg Arg Arg Xaa Xaa
 1               5                  10                  15

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence:membrane-
      translocating sequence (MTS)
<220> FEATURE:
<221> NAME/KEY: MOD_RES
<222> LOCATION: (12)
<223> OTHER INFORMATION: Xaa = aminohexanoic acid (aminocaproic acid)
<220> FEATURE:
<221> NAME/KEY: MOD_RES
<222> LOCATION: (22)
<223> OTHER INFORMATION: Xaa = aminohexanoic acid (aminocaproic acid)
<220> FEATURE:
<221> NAME/KEY: MOD_RES
<222> LOCATION: (23)
<223> OTHER INFORMATION: Xaa = tyrosinamide modified by 125-I

<400> SEQUENCE: 19

Glu Glu Glu Asp Asp Asp Glu Glu Glu Asp Ala Xaa Arg Arg Arg Arg
 1               5                  10                  15
```

Arg Arg Arg Arg Arg Xaa Xaa
         20

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:peptide
      linker cleavable by matrix metalloproteinase-9 (MMP-9)
<220> FEATURE:
<221> NAME/KEY: MOD_RES
<222> LOCATION: (3)
<223> OTHER INFORMATION: Xaa = Ser or Thr
<220> FEATURE:
<221> NAME/KEY: MOD_RES

```
<222> LOCATION: (4)
<223> OTHER INFORMATION: Xaa = Leu or Ile
<220> FEATURE:
<221> NAME/KEY: MOD_RES
<222> LOCATION: (5)
<223> OTHER INFORMATION: Xaa = Ser or Thr

<400> SEQUENCE: 29

Pro Arg Xaa Xaa Xaa
 1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:peptide
      linker cleavable by matrix metalloproteinase-11 (MMP-11)

<400> SEQUENCE: 30

Gly Gly Ala Ala Asn Leu Val Arg Gly Gly
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:peptide
      linker cleavable by matrix metalloproteinase-14 (MMP-14)

<400> SEQUENCE: 31

Ser Gly Arg Ile Gly Phe Leu Arg Thr Ala
 1               5                  10

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:peptide
      linker cleavable by urokinase plasminogen activator (uPA)

<400> SEQUENCE: 32

Ser Gly Arg Ser Ala
 1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:peptide
      linker cleavable by lysosomal enzymes

<400> SEQUENCE: 33

Gly Phe Leu Gly
 1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence:peptide
      linker cleavable by lysosomal enzymes

<400> SEQUENCE: 34

Ala Leu Ala Leu
```

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:peptide
      linker cleavable by cathepsin D
<220> FEATURE:
<221> NAME/KEY: MOD_RES
<222> LOCATION: (3)
<223> OTHER INFORMATION: Xaa = S-ethylcysteine

<400> SEQUENCE: 35

Pro Ile Xaa Phe Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence:peptide
      linker cleavable by cathepsin K

<400> SEQUENCE: 36

Gly Gly Pro Arg Gly Leu Pro Gly
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:peptide
      linker cleavable by prostate-specific antigen

<400> SEQUENCE: 37

His Ser Ser Lys Leu Gln
 1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence:peptide
      linker cleavable by Herpes simplex virus protease

<400> SEQUENCE: 38

Leu Val Leu Ala Ser Ser Ser Phe Gly Tyr
 1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence:peptide
      linker cleavable by HIV protease

<400> SEQUENCE: 39

Gly Val Ser Gln Asn Tyr Pro Ile Val Gly
 1               5                   10

<210> SEQ ID NO 40
<211> LENGTH: 10
<212> TYPE: PRT
```

```
<213> ORGANISM: Artificial Sequence
<220> FEATURE:
<223> OTHER INFORMATION: Description of Artificial Sequence:peptide
      linker cleavable by Cytomegalovirus protease

<400> SEQUENCE: 40

Gly Val Val Gln Ala Ser Cys Arg Leu Ala
 1               5                  10

<210> SEQ ID NO 41

<400> SEQUENCE: 41

000

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:peptide
      linker cleavable by caspase-3

<400> SEQUENCE: 42

Asp Glu Val Asp
 1

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence:peptide
      linker cleavable by interleukin 1beta converting enzyme

<400> SEQUENCE: 43

Gly Trp Glu His Asp Gly
 1               5

<210> SEQ ID NO 44

<400> SEQUENCE: 44

000

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:amino acid
      portion of compond (d) of Figure 17

<400> SEQUENCE: 45

Gly Arg Lys Lys Arg Arg Gln Arg Arg Arg Gly Tyr
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:amino acid
      portion of compond (e) of Figure 17

<400> SEQUENCE: 46

Ile Arg Arg Arg Lys Lys Leu Arg Arg Leu Lys
 1               5                  10
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:amino acid
      portion of compond (f) of Figure 17, R9, Arg9,
      peptide portion B, uptake sequence

<400> SEQUENCE: 47

Arg Arg Arg Arg Arg Arg Arg Arg Arg
 1               5

<210> SEQ ID NO 48

<400> SEQUENCE: 48

000

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence:fluorescent
      positive control membrane-translocating sequence
      (MTS) for uptake, abbreviated "R10"
<220> FEATURE:
<221> NAME/KEY: MOD_RES
<222> LOCATION: (1)
<223> OTHER INFORMATION: Xaa = Gly modified by fluorescein (Fl)
<220> FEATURE:
<221> NAME/KEY: MOD_RES
<222> LOCATION: (12)
<223> OTHER INFORMATION: Xaa = argininamide

<400> SEQUENCE: 49

Xaa Gly Arg Arg Arg Arg Arg Arg Arg Arg Arg Xaa
 1               5                  10

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence:basic
      portion B
<220> FEATURE:
<221> NAME/KEY: MOD_RES
<222> LOCATION: (10)..(16)
<223> OTHER INFORMATION: Xaa = Arg or absent

<400> SEQUENCE: 50

Arg Arg Arg Arg Arg Arg Arg Arg Arg Xaa Xaa Xaa Xaa Xaa Xaa Xaa
 1               5                  10                  15

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence:acidic
      portion A
<220> FEATURE:
<221> NAME/KEY: MOD_RES
<222> LOCATION: (4)
<223> OTHER INFORMATION: Xaa = sulfoserine
<220> FEATURE:
<221> NAME/KEY: MOD_RES
<222> LOCATION: (9)
<223> OTHER INFORMATION: Xaa = glutamatamine attached to nitrogen-bound
      cargo molecule
```

```
<400> SEQUENCE: 51

Glu Glu Glu Xaa Glu Glu Glu Glu Xaa
 1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence:acidic
      portion A
<220> FEATURE:
<221> NAME/KEY: MOD_RES
<222> LOCATION: (9)
<223> OTHER INFORMATION: Xaa = tyrosine attached to nitrogen-bound cargo
      molecule

<400> SEQUENCE: 52

Glu Glu Glu Glu Glu Glu Glu Glu Xaa
 1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence:acidic
      portion A
<220> FEATURE:
<221> NAME/KEY: MOD_RES
<222> LOCATION: (3)
<223> OTHER INFORMATION: Xaa = tetrafluorotyrosine
<220> FEATURE:
<221> NAME/KEY: MOD_RES
<222> LOCATION: (9)
<223> OTHER INFORMATION: Xaa = glutamic acid attached to nitrogen-bound
      cargo molecule

<400> SEQUENCE: 53

Glu Glu Xaa Glu Glu Ala Glu Glu Xaa
 1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence:basic
      portion B
<220> FEATURE:
<221> NAME/KEY: MOD_RES
<222> LOCATION: (1)
<223> OTHER INFORMATION: Xaa = 2'-sulfo-acetamido-isoleucine attached to
      sulfur-linked cargo molecule
<220> FEATURE:
<221> NAME/KEY: MOD_RES
<222> LOCATION: (11)
<223> OTHER INFORMATION: Xaa = lysine attached to nitrogen-bound cargo
      molecule

<400> SEQUENCE: 54

Xaa Arg Arg Arg Lys Lys Leu Arg Arg Leu Xaa
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence:basic
      portion B
```

```
<220> FEATURE:
<221> NAME/KEY: MOD_RES
<222> LOCATION: (1)
<223> OTHER INFORMATION: Xaa = lysinamide attached through alpha and
      epsilon nitrogen-bound cargo molecule
<220> FEATURE:
<221> NAME/KEY: MOD_RES
<222> LOCATION: (10)
<223> OTHER INFORMATION: Xaa = dodecaheptyl-arginine

<400> SEQUENCE: 55

Xaa Arg Arg Arg Arg Arg Arg Arg Arg Xaa
 1               5                  10

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:enterokinase
      substrate cleavage site

<400> SEQUENCE: 56

Asp Asp Asp Asp Lys
 1               5
```

PEPTIDES WHOSE UPTAKE BY CELLS IS CONTROLLABLE

CROSS-REFERENCE TO RELATED APPLICATIONS

This application is a continuation application and claims the benefit under 35 U.S.C. §120 of U.S. application Ser. No. 12/244,602, filed Oct. 2, 2008.

STATEMENT OF FEDERALLY-SPONSORED RESEARCH

This invention was made with government support under NS27177 awarded by National Institute of Health, under W81XWH-05-1-0183 awarded by the Army, and under DE-FG-03-01ER63276, awarded by Department of Energy. The government has certain rights in this invention.

BACKGROUND OF THE INVENTION

Field of the Invention

This invention pertains to compositions and methods for transporting material across cell membranes, and methods for making such compositions.

INTRODUCTION

Cell membranes delimit the outer boundaries of cells, and regulate transport into and out of the cell interior. Made primarily of lipids and proteins, they provide a hydrophilic surface enclosing a hydrophobic interior across which materials must pass before entering a cell. Although many small, lipophilic compounds are able to cross cell membranes passively, most compounds, particles and materials must rely on active Mechanisms in order to gain entry into a living cell.

Transmembrane Transport

Regulation of transport into and out of a cell is vital for its continued viability. For example, cell membranes contain ion channels, pumps, and exchangers capable of facilitating the transmembrane passage of many important substances. However, transmembrane transport is selective: in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

Over the last decade, peptide sequences that can readily enter a cell have been identified. For example, the Tat protein of the human immunodeficiency virus 1 (HIV-1) is able to enter cells from the extracellular environment (e.g., Fawell et al. P.N.A.S. 91:664-668 (1994)). Such uptake is reviewed in, for example, Richard et al., *J. Biol. Chem.* 278(1):585-590 (2003).

Such molecules that are readily taken into cells may also be used to carry other molecules into cells along with them. Molecules that are capable of facilitating transport of substances into cells have been termed "membrane translocation signals" (MTS) as described in Tung et al., *Advanced Drug Delivery Reviews* 55:281-294 (2003). The most important MTS are rich in amino acids such as arginine with positively charged side chains. Molecules transported into cell by such cationic peptides may be termed "cargo" and may be reversibly or irreversibly linked to the cationic peptides. An example of a reversible linkage is found in Zhang et al., *P.N.A.S.* 95:9184-9189 (1994)).

MTS molecules are discussed in, for example, Wender et al., *P.N.A.S.* 97:13003-13008 (2000); Hällbrink et al., *Biochim. Biophys. Acta* 1515:101-109 (2001); Derossi et al., *Trends in Cell Biology* 8:84-87 (1998); Rothbard et al., *J. Med. Chem.* 45:3612-3618 (2002); Rothbard et al., Nature Medicine 6(11):1253-1247 (2000); Wadia et al., *Curr. Opinion Biotech.* 13:52-56 (2002); Futaki et al; *Bioconj. Chem.* 12:1005-1011 (2001); Rothbard et al., U.S. Pat. No. 6,306,993; Frankel et al., U.S. Pat. No. 6,316,003; Rothbard et al., U.S. Pat. No. 6,495,663; and Monahan et al., U.S. Pat. No. 6,630,351. All patents and publications, both supra and infra, are hereby incorporated by reference in their entirety.

The uptake facilitated by MTS molecules is typically without specificity, enhancing uptake into most or all cells. Thus, although MTS molecules are capable of entering cells, and may be capable of enhancing the transport of other molecules linked to MTS molecules into cells, control and regulation of such transport remains difficult. However, it would be desirable to have the ability to target the delivery of cargo to a type of cell, or to a tissue, or to a location or region within the body of an animal. Accordingly, there remains a need in the art to target, to control and to regulate the delivery of cargo molecules by MTS molecules.

SUMMARY OF THE INVENTION

Molecules, compositions and methods for controlled delivery of substances into cells by transport molecules are provided. Molecules having features of the invention include peptide portions linked by a cleavable linker portion which may be a peptide. The inventors have found that the cellular uptake of MTS molecules with multiple basic amino acids can be inhibited or prevented by the addition of a portion having multiple negative charges at physiological pH, such as a peptide portion having multiple acidic amino acids. Thus; an embodiment of the invention provides compounds including a peptide portion A of between about 2 to about 20 acidic amino acids linked by a cleavable linker X to a peptide portion B of between about 5 to about 20 basic amino acids, so that while the peptide portion A is linked to the peptide portion B, uptake of the molecule into cells is inhibited or prevented. An acidic, portion A may include some amino acids that are not acidic amino acids, or other moieties as well; similarly, a basic portion B may include some amino acids that are not basic amino acids, or other moieties as well. The inhibition or prevention of uptake of a basic portion B by an acidic portion A is termed "veto" of uptake of B. After cleavage of linker X so that peptide portion A may separate from the peptide portion B, portion B is able to enter a cell, the veto due to portion A having been removed. A cleavable linker X is preferably cleavable under physiological conditions.

In a further embodiment, a cargo portion C including a cargo moiety may be attached to basic portion B for transport of a cargo portion C along with B into a cell. Thus, an embodiment of the invention provides compounds including a Peptide portion A of between about 2 to about 20 acidic amino acids in sequence linked by a cleavable linker X to a peptide portion B of between about 5 to about 20 basic amino acids, the peptide portion B being covalently attached to a cargo portion C to form a structure C, effective that while the peptide portion A is linked to the portion B, uptake of the MTS compound into cells is inhibited or prevented. Acidic portion A is able to veto of uptake of B-C. Transport across a cell membrane of cargo portion C linked to portion B is also thus inhibited or prevented by acidic portion A. After cleavage of linker X so that peptide portion A may separate from the peptide portion B, cargo portion C linked to peptide portion B is able to enter a cell as the uptake veto due to peptide portion A has been removed. A cleavable linker X is preferably cleavable under physiological conditions, allowing transport of cargo portion C into living cells. Cargo portion C may also be cleavably attached to basic portion B so that cargo portion C may separate from portion B within a cell.

Thus, an embodiment of the invention provides molecules including a peptide portion A having multiple acidic amino acids, e.g., between about 2 to about 20, preferably between about 5 and 20 acidic amino acids, the peptide portion A being effective to prevent the uptake of an MTS molecule having a peptide portion B having multiple basic amino acids e.g., between about 5 to about 20, preferably between about 9 to about 16 basic amino acids. Peptide portion A is also thus effective to prevent the enhancement of transport of cargo C across a cell membrane by a peptide portion B having multiple basic amino acids. Cleavage of a peptide portion A from a molecule that has a peptide portion B is effective to restore the ability of the remaining portion of the molecule including the portion B to be taken up by a cell. Cleavage of a peptide portion A from a molecule that has a cargo portion C covalently attached to a peptide portion B to form a structure B-C is effective to restore the ability of the structure B-C to be taken up by a cell.

In one embodiment, a molecule for controllably transporting a cargo moiety across a cell membrane includes a molecule or material having the structure A-X-B-C, where C comprises a cargo moiety, B comprises a peptide portion having multiple basic amino acids (e.g., between about 5 to about 20, preferably between about 9 to about 16 basic amino acids), B and C being covalently linked, A comprises a peptide portion having multiple acidic amino acids (e.g., between about 2 to about 20, preferably between about 4 to about 20 acidic amino acids), and X comprises a cleavable linker joining A with B-C. When linked with B-C, peptide portion A is effective to prevent the enhancement of transport of cargo C across a cell membrane. When the cleavable linker X is cleaved, the peptide portion A is freed from the rest of the molecule, including being freed from portion B and cargo portion C. The cargo portion C remains linked to portion B after cleavage of the cleavable linker X. The portion B is effective to enhance transport of Cargo portion C across a cell membrane in the absence of portion A.

In embodiments of the invention, including molecules having the schematic structure A-X-B and molecules having the schematic structure A-X-B-C, acidic amino acids of portion A are glutamate, aspartate, or phosphoserine. An acidic amino acid has a side chain with a negative charge at pH 6.0, and may be glutamic acid, aspartic acid, or other acidic amino acid. An acidic portion A having multiple acidic amino acids may have between about 2 to about 20, or between about 5 to about 20, or preferably from about 5 to about 9 acidic amino acids. In preferred embodiments, portion A comprises 5 to 9 glutamates or aspartates, and may comprise 5 to 9 consecutive glutamates or aspartates. In embodiments, acidic amino acids of portion A are D amino acids. In preferred embodiments, acidic amino acids of portion A are either D-glutamate, D-aspartate, or both.

A basic amino acid has a side chain with a positive charge at pH 6.0, and may be arginine, histidine, lysine, or other basic amino acid. In embodiments of the invention, the basic amino acids of portion B are either arginine, lysine or histidine. A basic portion B having multiple basic amino acids may have between about 5 to about 20, or between about 9 to about 16 basic amino acids. In preferred embodiments, portion B comprises about 9 to about 16 arginines, and may comprise about 9 to about 16 consecutive arginines (SEQ ID NO:50). In embodiments of the invention, the basic amino acids of portion B are D amino acids. In preferred embodiments, basic amino acids of portion B are either D-arginine, D-lysine, D-histidine, or combinations thereof.

A cargo moiety may be any molecule, material, substance, or construct that may be transported into a cell by linkage to a MTS. A cargo portion C may include one or more cargo moieties. A cargo moiety may be, for example, a fluorescent moiety, a fluorescence-quenching moiety, a radioactive moiety, a radiopaque moiety, a paramagnetic moiety, a nanoparticle, a vesicle, a molecular beacon, a marker, a Marker enzyme (e.g., horse-radish peroxidase (HRP), beta-galactosidase, or other enzyme suitable for marking a cell), a contrast agent (e.g., for diagnostic imaging), a chemotherapeutic agent, a radiation-sensitizer (e.g., for radiation therapy), a peptide or protein that affects the cell cycle, a protein toxin, or other cargo suitable for transport into a cell. In some embodiments where C is a fluorescent moiety, a fluorescence-quenching moiety is attached to portion A effective to quench the fluorescence of the fluorescent moiety C before cleavage of the linker X, and removing the quenching of fluorescent moiety C after cleavage of linker X.

A cleavable linker X serves to connect an acidic portion A with a basic portion B. A cleavable linker X may include, for example, between about 2 to about 100 atoms, or between about 6 to about 30 atoms. Cleavable linker portion X may include amino acid, residues, and may be a peptide linkage of between about 1 to about 30, or between about 2 to about 10 amino acid residues. A cleavable linker X suitable for the practice of the invention may be a flexible linker. In preferred embodiments, a cleavable linker X suitable for the practice of the invention is a flexible linker, and may be about 6 to about 24 atoms in length. In embodiments of the invention, X may include a peptide linkage. In some preferred embodiments of the invention, a cleavable linker X includes aminocaproic acid.

A cleavable linker X may be configured for cleavage exterior to a cell. In preferred embodiments of the invention, a cleavable linker X may be configured to be cleaved in conditions associated with cell or tissue damage or disease. Such conditions include, for example, acidosis; the presence of intracellular enzymes (that are normally confined within cells), including necrotic conditions (e.g., cleaved by calpains or other proteases that spill out of necrotic cells); hypoxic conditions such as a reducing environment; thrombosis (e.g., a linker X may be cleavable by thrombin or by another enzyme associated with the blood clotting cascade); immune system activation (e.g., a linker X may be cleavable by action of an activated complement protein); or other condition associated with disease or injury.

For example, a cleavable linker X may be configured for cleavage by an enzyme, such as a matrix metalloprotease. Other enzymes which may cleave a cleavable linker include, for example, urokinase plasminogen activator (uPA), lysosomal enzymes, cathepsins, prostate-specific antigen, Herpes simplex virus protease, cytomegalovirus protease, thrombin, caspase, and interleukin 1β converting enzyme. In embodiments of the invention, cleavable linker X may include the amino acid sequence PLGLAG (SEQ ID NO:1) or may include the amino acid sequence EDDDDKA (SEQ ID NO:2). In other embodiments, a cleavable linker X may include a S—S linkage, or may include a transition metal complex that falls apart when the metal is reduced. A molecule embodying features of the invention may have multiple linkers X linking a plurality of portions A having acidic amino acids to a structure B-C.

In embodiments of the invention, peptide portion A is located at a terminus of a polypeptide chain comprising B-C, or comprises the amino terminus of a polypeptide chain comprising B-C. A may be linked near to or at the amino terminus of a polypeptide chain comprising B-C, or A may be linked near to or at the carboxy terminus of a polypeptide chain comprising B-C. The Polypeptide chain B-C may have ends that may be termed a B-side terminus and a C-side terminus. A cleavable linker X may be disposed near or at the B-side terminus, or may be disposed near or at the C-side terminus. In further embodiments, a portion or portions may be linear or may be cyclic. In embodiments, a cyclic molecule having features of the invention may have a single linker X or may have multiple linkers X.

In further embodiments of the invention, compositions and solutions, including pharmaceutical compositions are provided which include compounds of the invention having peptides capable of controllable delivery of cargo into a cell and a suitable carrier. Methods for producing such peptides capable of controllable delivery of cargo into a cell, and pharmaceutical compositions containing them are also provided. It will be understood that, in embodiments of the invention, peptoids, carbamates, vinyl polymers, and other molecules, with a cleavable linkage between an acidic and a basic portion, may also be provided.

The molecules, compositions and methods embodying features of the invention provide the advantages of controlling the uptake of basic amino acid-containing molecules into cells, and of controlling the delivery of cargo into cells. Such controlled uptake and controlled delivery of cargo into cells may be useful, for example, in treatment of patients having diseased cells or tissues. For example, delivery of an imaging contrast agent or antiproliferative agent as cargo may be directed to cancer cells, and not to all cells in a patient, offering the advantage of targeted delivery to the diseased cells, in order to enable noninvasive imaging or increase the effectiveness and decrease possible side effects of the treatment.

BRIEF DESCRIPTION OF THE DRAWINGS

FIG. 6A illustrates a High Pressure Liquid Chromatography (HPLC) chromatogram of a peptide having features of the invention before cleavage of linker portion X that is a substrate for enterokinase.

FIG. 6B illustrates a HPLC chromatogram of the peptide of FIG. 6A after cleavage of linker portion X by enterokinase.

DETAILED DESCRIPTION OF THE INVENTION

Figure 1A:
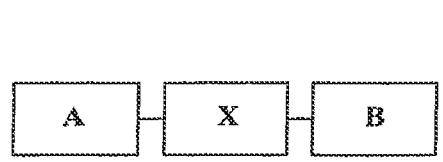
FIG. 1A is a schematic representation of a MTS molecule having features of the invention comprising a basic portion B, a linker portion X, and an acidic portion A.
Figure 1B:
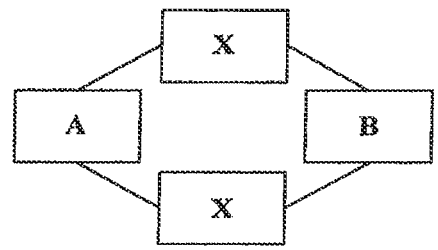
FIG. 1B is a schematic representation of a cyclic MTS molecule having features of the invention comprising a basic portion B, two linker portions X, and an acidic portion A.

In one embodiment, a generic structure for peptides having features of the invention is A-X-B, where peptide portion B includes between about 5 to about 20 basic amino acids, X is a cleavable linker portion, preferably cleavable under physiological conditions, and where peptide portion A includes between about 2 to about 20 acidic amino acids. In some embodiments of molecules having features of the invention, peptide portion B includes between about 5 to about 20, or between about 9 to about 16 basic amino acids, and may be a series of basic amino acids (e.g., arginines, histidines, lysines, or other basic amino acids). In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). A schematic representation of a MTS molecule having features of the invention comprising a basic portion B, a linker portion X, and an acidic portion A is presented in FIG. 1A. In embodiments, MTS molecules having features of the invention may be cyclic molecules, as schematically illustrated in FIG. 1B. Thus, MTS molecules having features of the invention may be linear molecules, cyclic molecules, or may be linear molecules including a cyclic portion.

As discussed above, molecules including a multiple basic amino acids, such as a series of basic amino acids, are often taken up by cells. However, the present inventors have discovered that molecules having structures including a basic portion B, a linker portion X, and an acidic portion A are not taken up by cells. An acidic portion A may include amino acids that are not acidic. Acidic portion A may comprise other moieties, such as negatively charged moieties. In embodiments of MTS molecules having features of the invention, an acidic portion A may be a negatively charged portion, preferably having about 2 to about 20 negative charges at physiological pH, that does not include an amino acid. A basic portion B may include amino acids that are not basic. Basic portion B may comprise other moieties, such as positively charged moieties. In embodiments of MTS molecules having features of the invention, a basic portion B may be a positively charged portion, preferably having between about 5 and about 20 positive charges at physiological pH, that does not include an amino acid. Including an acidic portion A is effective to inhibit or prevent the uptake of a portion B into cells. Such a block of uptake that would otherwise be effected by the basic amino acids of portion B may be termed a "veto" of the uptake by the acidic portion A. The present inventors have made the further surprising discovery that cleavage of linker X, allowing the separation of portion A from portion B is effective to allow the uptake of portion B into cells.

In a further embodiment, a generic structure for peptides having features of the invention is A-X-B-C, where C is a cargo moiety, X a linker, A an acidic portion, and B a basic portion. An acidic portion A may include amino acids that are not acidic. Acidic portion A may comprise other moieties, such as negatively charged moieties. In embodiments of MTS molecules having features of the invention, an acidic portion A may be a negatively charged portion, preferably having about 2 to about 20 negative charges at physiological pH, that does not include an amino acid. A basic portion B may include amino acids that are not basic. Basic portion B may comprise other moieties, such as positively charged moieties. In embodiments of MTS molecules having features of the invention, a basic portion B may be a positively charged portion, preferably having between about 5 and about 20 positive charges at physiological pH, that does not include an amino acid. In preferred embodiments, the amount of negative charge in portion A is approximately the same as the amount of positive charge in portion B.

A cargo moiety C may be, for example, a contrast-agent for diagnostic imaging, or a chemotherapeutic drug or radiation-sensitizer for therapy. B may be, for example, a peptide portion having between about 5 to about 20 basic amino acids, such as a series of basic amino acids (arginines are preferred, although histidines are also suitable, as are lysines or other basic amino acids). X is a cleavable linker that is preferably cleavable under physiological conditions. A may be a peptide portion having between about 2 to about 20 about 2 to about 20 acidic amino acids, such as a series of acidic amino acids. In some embodiments of molecules having features of the invention, glutamates and aspartates are preferred acidic amino acids for peptide portion A. A schematic representation of a MTS molecule having features of the invention comprising a cargo portion C, a basic portion B, a linker portion X, and an acidic portion A is presented in FIG. 2A.

The present inventors have made the surprising discovery that including an acidic portion A is also effective to inhibit or prevent the uptake into cells of molecules combining a portion B and a portion C. The present inventors have made the further discovery that cleavage of linker X, allowing the separation of portion A from portion B is effective to allow the uptake of portions B and C into cells. Thus, delivery of cargo C can be controlled and enhanced by molecules having features of the invention.

For example, when peptide portion A contains about 5 to about 9 consecutive glutamates or aspartates, and X is a flexible linker of about 2 to about 100, or about 6 to about 30 atoms in length, the normal ability of a peptide portion B (e.g., a sequence of nine consecutive arginine residues SEQ ID NO:47) to cause uptake into cells is blocked. Cleavage of linker X allows the separation of portion A from portion B and portion C, alleviating the veto by portion A. Thus, when separated from A, the normal ability of portion B to effect the uptake of cargo C into cells is regained. Such cellular uptake typically occurs near the location of the cleavage event. Thus, design of cleavable linker X such that it is cleaved at or near a target cell is effective to direct uptake of cargo C into target cells. Extracellular cleavage of X allows separation of A from the rest of the molecule to allow uptake into cells.

A MTS molecule having features of the invention may be of any length. In embodiments of MTS molecules having features of the invention, a MTS molecule may be about 7 to about 40 amino acids in length, not including the length of a linker X and a cargo portion C. In other embodiments, particularly where multiple non-acidic (in portion A) or non-basic (in portion B) amino acids are included in one or both of portions A and B, portions A and B of a MTS molecule may together be about 50, or about 60, or about 70 amino acids in length. A cyclic portion of an MTS may include about 12 to about 60 amino acids, not including the length of a linker X and a cargo portion C. For example, a linear MTS molecule having features of the invention may have a basic portion B having between about 5 to about 20 basic amino acids (preferably between about 9 to about 16 basic amino acids) and an acidic portion A having between about 2 to about 20 acidic amino acids (e.g., between about 5 to about 20, preferably between about 5 to about 9 acidic amino acids). In some preferred embodiments, a MTS molecule having features of the invention may have a basic portion B having between about 9 to about 16 basic amino acids and between about 5 to about 9 acidic amino acids.

In healthy cells, the intact compound of structure A-X-B or A-X-B-C would not be able to enter the cell because of the presence of portion A. Thus, a strictly intracellular process for cleaving X would be ineffective to cleave X in healthy cells since portion A, preventing uptake into cells, would not be effectively cleaved by intracellular enzymes in healthy cells since it would not be taken up and would not gain access to such intracellular enzymes. However, where a cell is injured or diseased, so that such intracellular enzymes leak out of the cell, cleavage of A would occur, allowing entry of portion B or B-C into the cell, effecting targeted delivery of portion B or of cargo portion C to neighboring cells.

Portions A and B may include either L-amino acids or amino acids. In embodiments of the invention, D-amino acids are preferred for the A and B portions in order to minimize immunogenicity and nonspecific cleavage by background peptidases or proteases. Cellular uptake of oligo-D-arginine sequences is known to be as good or better than that of oligo-L-arginines. The generic structures A-X-B and -A-X-B-C can be effective where A is at the amino terminus and where A is at the carboxy terminus, i.e. either orientation of the peptide bonds is permissible. However, in embodiments where X is a peptide cleavable by a protease, it may be preferable to join the C-terminus of X to the N-terminus of B, so that the new amino terminus created by cleavage of X contributes an additional positive charge that adds to the positive charges already present in B.

Figure 2A:
FIG. 2A is a schematic representation of a MTS molecule having features of the invention comprising a cargo portion C, a basic portion B, a linker portion X, and an acidic portion A.
Figure 2B:
FIG. 2B is a schematic representation of a MTS molecule having features of the invention comprising a cargo portion C, a basic portion B, a linker portion X, and an acidic portion A, the linker portion X connecting to the cargo portion C.
Figure 2C:
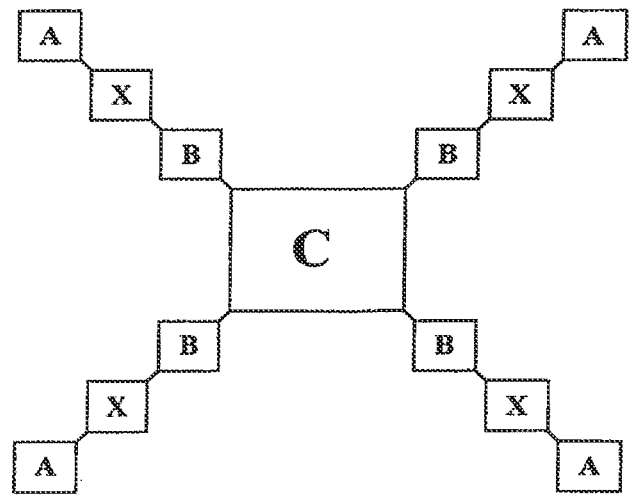
FIG. 2C is a schematic representation of a MTS molecule having features of the invention comprising a cargo C linked to multiple copies of MTS molecules each comprising a basic portion B, a linker portion X, and an acidic portion A.

Cargo portion C may be attached to B in any location or orientation. A cargo portion C need not be located at an opposite end of portion B than a linker X. Any location of attachment of C to B is acceptable as long as that attachment remains after X is cleaved. For example, a cargo portion C may be attached to or near to an end of portion B with linker X attached to an opposite end of portion B as illustrated in FIGS. 2A and 2B. A cargo portion C may also be attached to or near to an end of portion B with linker X attached to or near to the same end of portion B. In some embodiments of the invention, a linker X may link to a cargo portion C which is linked to a basic portion B as illustrated in FIG. 2B. FIG. 2C is a schematic representation of a MTS molecule having features of the invention comprising a cargo portion C linked to multiple basic portions B, each of which basic portions B are linked to a linker portion X, and via the linker to an acidic portion A.

A linker X may be designed for cleavage in the presence of particular conditions or in a particular environment. In preferred embodiments, a linker X is cleavable under physiological conditions. Cleavage of such a linker X may, for example, be enhanced or may be effected by particular pathological signals or a particular environment related to cells in which cargo delivery is desired. The design of a linker X for cleavage by specific conditions, such as by a specific enzyme, allows the targeting of cellular uptake to a specific location where such conditions obtain. Thus, one important way that MTS molecules having features of the invention provide specific targeting of cellular uptake to desired cells, tissues, or regions is by the design of the linker portion X to be cleaved by conditions near such targeted cells, tissues, or regions. After cleavage of a linker X, the portions B-C of the molecule are then a simple conjugate of B and C, in some instances retaining a relatively small, inert stub remaining from a residual portion of linker X.

A linker portion X may be cleavable by conditions found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. Other examples of pH-sensitive linkages include acetals, ketals, activated amides such as amides of 2,3 dimethylmaleamic acid, vinyl ether, other activated ethers and esters such as enol or silyl ethers or esters, imines, iminiums, enamines, carbamates, hydrazones, and other linkages. A linker X may be an amino acid or a peptide. A peptide linker may be of any suitable length, such as, for example, about 3 to about 30, or preferably about 6 to about 24 atoms in sequence (e.g., a linear peptide about 1 to 10 or preferably about 2 to 8 amino acids long). A cleavable peptide linker may include an amino acid sequence recognized and cleaved by a protease, so that proteolytic action of the protease cleaves the linker X.

One important class of signals is the hydrolytic activity of matrix metalloproteinases (MMPs), which are very important in the invasive migration of metastatic tumor cells. MMPs are also believed to play major roles in inflammation and stroke. MMPs are reviewed in Visse et al., *Circ. Res.* 92:827-839 (2003). MMPs may be used to cleave a linker X and so to allow separation of acidic portion A from portions B and C, allowing cellular uptake of cargo C so that cellular uptake of C is triggered by action of MMPs. Such uptake is typically in the vicinity of the MMPs that trigger cleavage of X. Thus, uptake of molecules having features of the invention are able to direct cellular uptake of cargo C to specific cells, tissues, or regions having active MMPs in the extracellular environment.

For example, a linker X that includes the amino-acid sequence PLGLAG (SEQ ID NO: 1) may be cleaved by the metalloproteinase enzyme MMP-2 (a major MMP in cancer and inflammation). Cleavage of such a linker X occurs between the central G and L residues, causing cell uptake to increase by 10 to 20-fold (see Example 4). A great deal is known about the substrate preferences of different MMPs, so that linkers X may be designed that are able to bias X to be preferentially sensitive to particular subclasses of MMPs, or to individual members of the large MMP family of proteinases. For example, in some embodiments, linkers X designed to be cleaved by membrane-anchored MMPs are particularly preferred because their activity remains localized to the outer surface of the expressing cell. In alternative embodiments, linkers X designed to be cleaved by a soluble secreted MMP are preferred where diffusion of cargo C away from the exact location of cleavage may be desired, thereby increasing the spatial distribution of the cargo. Other linkers X cleavable by other MMPs are discussed in Example 9.

Hypoxia is an important pathological signal. For example, hypoxia is thought to cause cancer cells to become more resistant to radiation and chemotherapy, and also to initiate angiogenesis. A linker X suitable for cleavage in or near tissues suffering from hypoxia enables targeting of portion B and C to cancer cells and cancerous tissues, infarct regions, and other hypoxic regions. For example, a linker X that includes a disulfide bond is preferentially cleaved in hypoxic regions and so targets cargo delivery to cells in such a region. In a hypoxic environment in the presence of, for example, leaky or necrotic cells, free thiols and other reducing agents become available extracellularly, while the $O_2$ that normally keeps the extracellular environment oxidizing is by definition depleted. This shift in the redox balance should promote reduction and cleavage of a disulfide bond within a linker X. In addition to disulfide linkages which take advantage of thiol-disulfide equilibria, linkages including quinones that fall apart when reduced to hydroquinones may be used in a linker X designed to be cleaved in a hypoxic environment.

Necrosis often leads to release of enzymes or other cell contents that may be used to trigger cleavage of a linker X. A linker X designed for cleavage in regions of necrosis in the absence of hypoxia, for example, may be one that is cleaved by calpains or other proteases that may be released from necrotic cells. Such cleavage of linkers X by calpains would release the connected portions B-C from portion A, allowing cargo to be taken up by diseased cells and by neighboring cells that had not yet become fully leaky.

Acidosis is also commonly observed in sites of damaged or hypoxic tissue, due to the Warburg shift from oxidative phosphorylation to anaerobic glycolysis and lactic acid production. Such local acidity could be sensed either by making an acid-labile linker X (e.g., by including in X an acetal or vinyl ether linkage). Alternatively, or in addition, acidosis may be used as a trigger of cargo uptake by replacing some of the arginines within B by histidines, which only become cationic below pH 7.

Molecules having features of the invention are suitable for carrying different cargoes, including different types of cargoes and different species of the same types of cargo, for uptake into cells. For example, different types of cargo may include marker cargoes (e.g., fluorescent or radioactive label moieties) and therapeutic cargoes (e.g., chemotherapeutic molecules such as methotrexate or doxorubicin), or other cargoes. Where destruction of aberrant or diseased cells is therapeutically required, a therapeutic cargo may include a "cytotoxic agent," i.e. a substance that inhibits or prevents the function of cells and/or causes destruction of cells. In some embodiments, a single molecule having features of the invention may include more than one cargo portion C so that a basic portion B may be linked to multiple cargoes C. Such multiple cargoes C may include marker cargoes, therapeutic cargoes, or other cargoes. Multiple cargo moieties may allow, for example, delivery of both a radioactive marker and an ultrasound or contrast agent, allowing imaging by different modalities. Alternatively, for example, delivery of radioactive cargo along with an anti-cancer agent, providing enhanced anticancer activity, or delivery of a radioactive cargo with a fluorescent cargo, allowing multiple means of localizing and identifying cells which have taken up cargo.

Delivery of cargo such as a fluorescent molecule may be used to visualize cells having a certain condition or cells in a region exhibiting a particular condition. For example, thrombosis (clot formation) may be visualized by designing a linker X to be cleaved by any of the many proteases in the blood clot formation cascade for delivery of a cargo including a fluorescent or other marker to the region. Similarly, complement activation may be visualized by designing a linker X to be cleaved by any one or more of the proteases in the complement activation cascades for delivery of a fluorescent or other marker to the region. Thus, fluorescent molecules are one example of a marker that may be delivered to target cells and regions upon release of a portion A upon cleavage of a linker X.

Figure 2D:
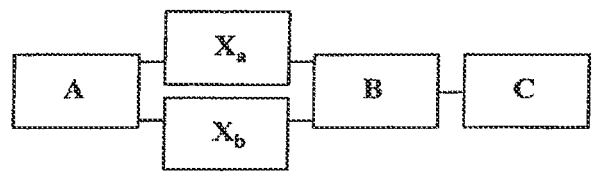
FIG. 2D is a schematic representation of a MTS molecule having features of the invention comprising a cargo portion C, a basic portion B, multiple (two) linker regions X, and an acidic portion A.
Figure 2E:
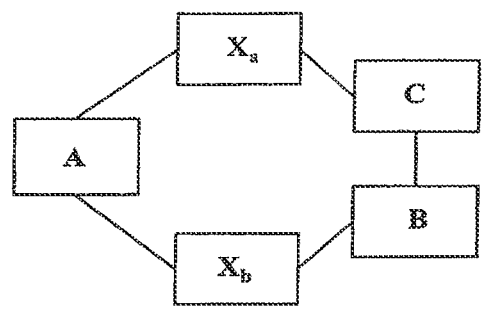
FIG. 2E is a schematic representation of a cyclic MTS molecule having features of the invention comprising a cargo portion C, a basic portion B, in which two linker regions X flank an acidic portion. A.

A molecule having features of the invention may include one or more linkers X so that an acidic portion A may be linked to portions B and C by one or more linkages. Such linkages connecting to portion A may be to portion B, to portion C, or to both portions B and C. Where a molecule having features of the invention includes multiple linkages X, separation of portion A from the other portions of the molecule requires cleavage of all linkages X. Cleavage of multiple linkers X may be simultaneous or sequential. Multiple linkages X may include linkages X having different specificities, so that separation of portion A from the other portions of the molecule requires that more than one condition or environment ("extracellular signals") be encountered by the molecule. Cleavage of multiple linkers X thus serves as a detector of combinations of such extracellular signals. FIG. 2D shows a MTS molecule having features of the invention that includes two linker portions Xa and Xb connecting basic portion B with acidic portion A. FIG. 2E shows a cyclic MTS molecule having features of the invention that includes two linker regions Xa and Xb connecting basic portion B with acidic portion A. In the MTS molecules schematically illustrated in FIGS. 2D and 2E, both linkers Xa and Xb must be cleaved before acidic portion A is separated from basic portion B allowing entry of portion B and cargo portion C (if any) to enter a cell. It will be understood that a linker region may link to either a basic portion B or a cargo portion C independently of another linker that may be present, and that, where desired, more than two linker regions X may be included.

Combinations of two or more linkers X may be used to further modulate the targeting and delivery of molecules to desired cells, tissue or regions. Boolean combinations of extracellular signals can be detected to widen or narrow the specificity of the cleavage of linkers X if desired. Where multiple linkers X are linked in parallel, the specificity of cleavage is narrowed, since each linker X must be cleaved before portion A may separate from the remainder of the molecule. Where multiple linkers X are linked in series, the specificity of cleavage is broadened, since cleavage on any one linker X allows separation of portion A from the remainder of the molecule. For example, in order to detect either a protease OR hypoxia (i.e., to cleave X in the presence of either protease or hypoxia), a linker X is designed to place the protease-sensitive and reduction sensitive sites in tandem, so that cleavage of either would suffice to allow separation of the acidic portion A. Alternatively, in order to detect the presence of both a protease AND hypoxia (i.e., to cleave X in the presence of both protease and hypoxia but not in the presence of only one alone), a linker X is designed to place the protease sensitive site between at least one pair of cysteines that are disulfide-bonded to each other. In that case, both protease cleavage AND disulfide reduction are required in order to allow separation of portion A.

The fact that capillaries are often leaky around tumors and other trauma sites should enhance the ability of high molecular weight molecules (e.g., molecular weight of about 40 kDa or more) to reach the interstitial compartment. Since the cleavage of a linker X is typically extracellular, some bystander labeling is expected, i.e. cells that do not express the relevant protease but that are immediately adjacent to expressing cells are likely to pick up some of the cargo. For tumors, such bystander targeting is considered beneficial because of the heterogeneity of cell phenotypes and the wish to eliminate as high a percentage of suspicious cells.

The fact that a single mechanism can mediate uptake of both imaging and therapeutic cargoes will be particularly valuable, because imaging with noninjurious tracer quantities can be used to test whether a subsequent therapeutic dose is likely to concentrate correctly in the target tissue.

Figure 3:
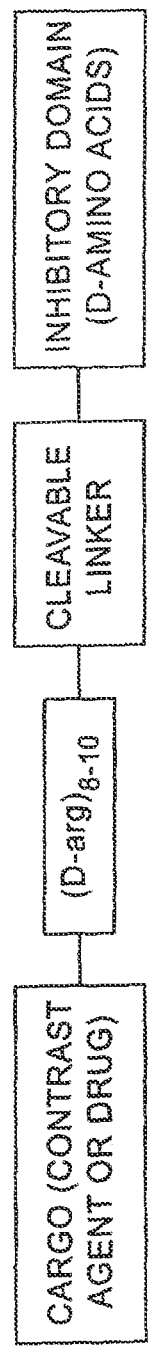
FIG. 3 is a schematic representation of a MTS molecule having features of the invention in which a cargo portion C is a contrast agent or drug, a basic portion B is a sequence of eight to ten D-arginine residues, a linker portion X is a cleavable linker that may be cleaved by proteolytic enzymes or reducing environment found near cancerous cells, and an acidic portion A is an inhibitory domain comprising D-amino acids.

D amino acids may be used in MTS molecules having features of the invention. For example, some or all of the peptides of portions A and B may be D-amino acids in some preferred embodiments of the invention. In an embodiment of the invention suitable for delivering a detectable marker to a target cell, a MTS having features of the invention includes a contrast agent as cargo C attached to a basic portion B comprising 8 to 10 D-arginines. Acidic portion A may include D-amino acids as well. Similarly, a drug may be delivered to a cell by such molecules having a basic portion B including 8 to 10 D-arginines and an acidic portion A including acidic D-amino acids. A schematic representation of such MTS molecules is shown in FIG. 3.

It will be understood that a MTS molecule having features of the invention may include non-standard amino acids, such as, for example, hydroxylysine, desmosine, isodesmosine, or other non-standard amino acids. A MTS molecule having features of the invention may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A MTS molecule having features of the invention may also include peptide mimetic moieties, including portions linked by non-peptide bonds and amino acids linked by or to non-amino acid portions. For example, a MTS molecule having features of the invention may include peptoids, carbamates, vinyl polymers, or other molecules having non-peptide linkages but having an acidic portion cleavably linked to a basic portion having a cargo moiety.

Figure 4:
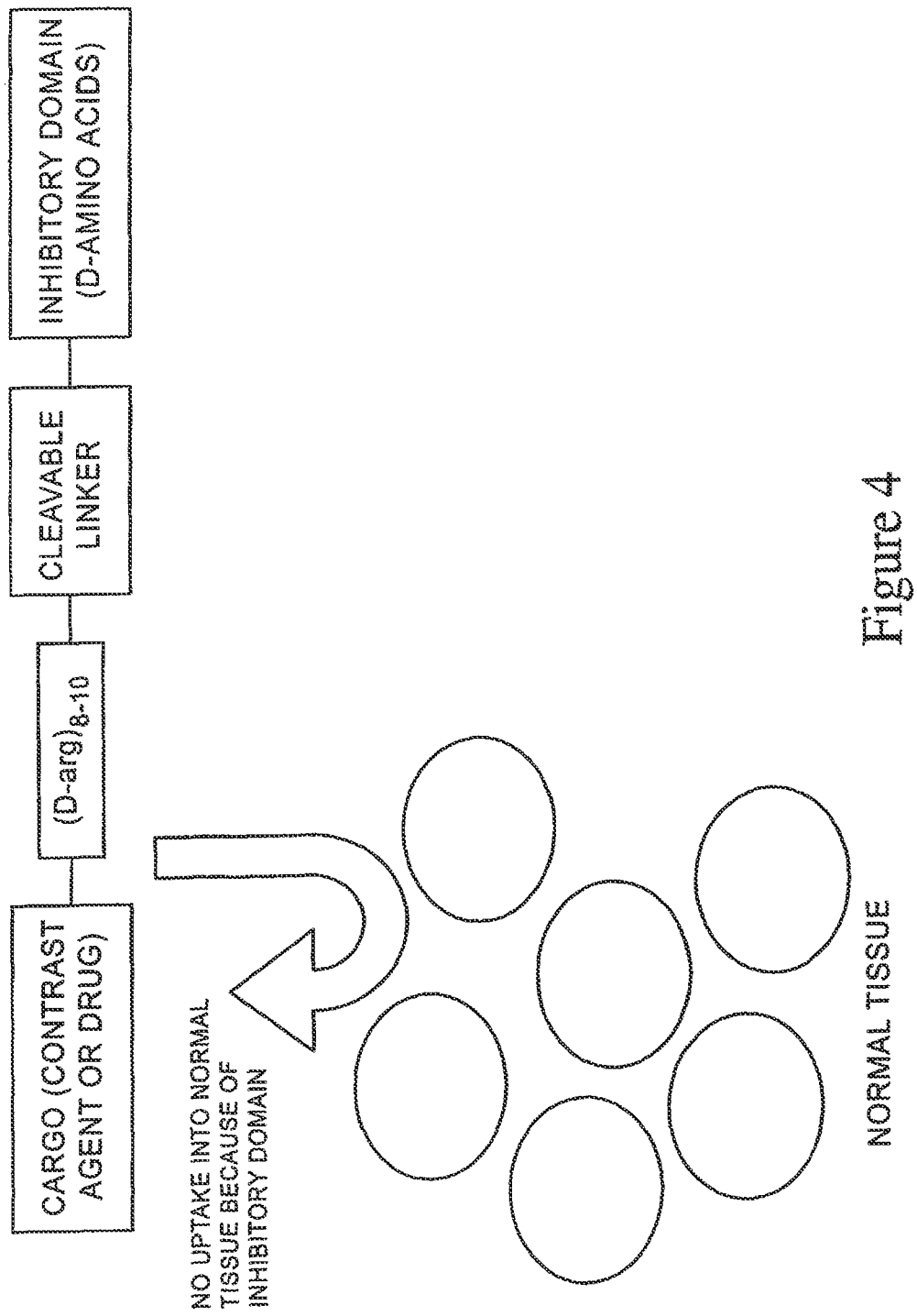
FIG. 4 is a schematic representation of a MTS molecule of FIG. 3 having features of the invention in which the cleavable linker is not cleaved near normal tissue, showing the inability of a molecule of FIG. 3 to facilitate the entry of cargo into normal tissue.

The linker portion X may be designed so that it is cleaved, for example, by proteolytic enzymes or reducing environment, as may be found near cancerous cells. Such an environment, or such enzymes, are typically not found near normal cells. FIG. 4 illustrates a MTS molecule as shown in FIG. 3, having a cleavable linker X designed to be cleaved near cancerous cells. As illustrated in FIG. 4, the cleavable linker is not cleaved near normal tissue. FIG. 4 illustrates the ability of a MTS having a portion A capable of vetoing cellular uptake of a portion B, and of a portion B-C, blocking the entry of cargo into normal tissue.

Figure 5:
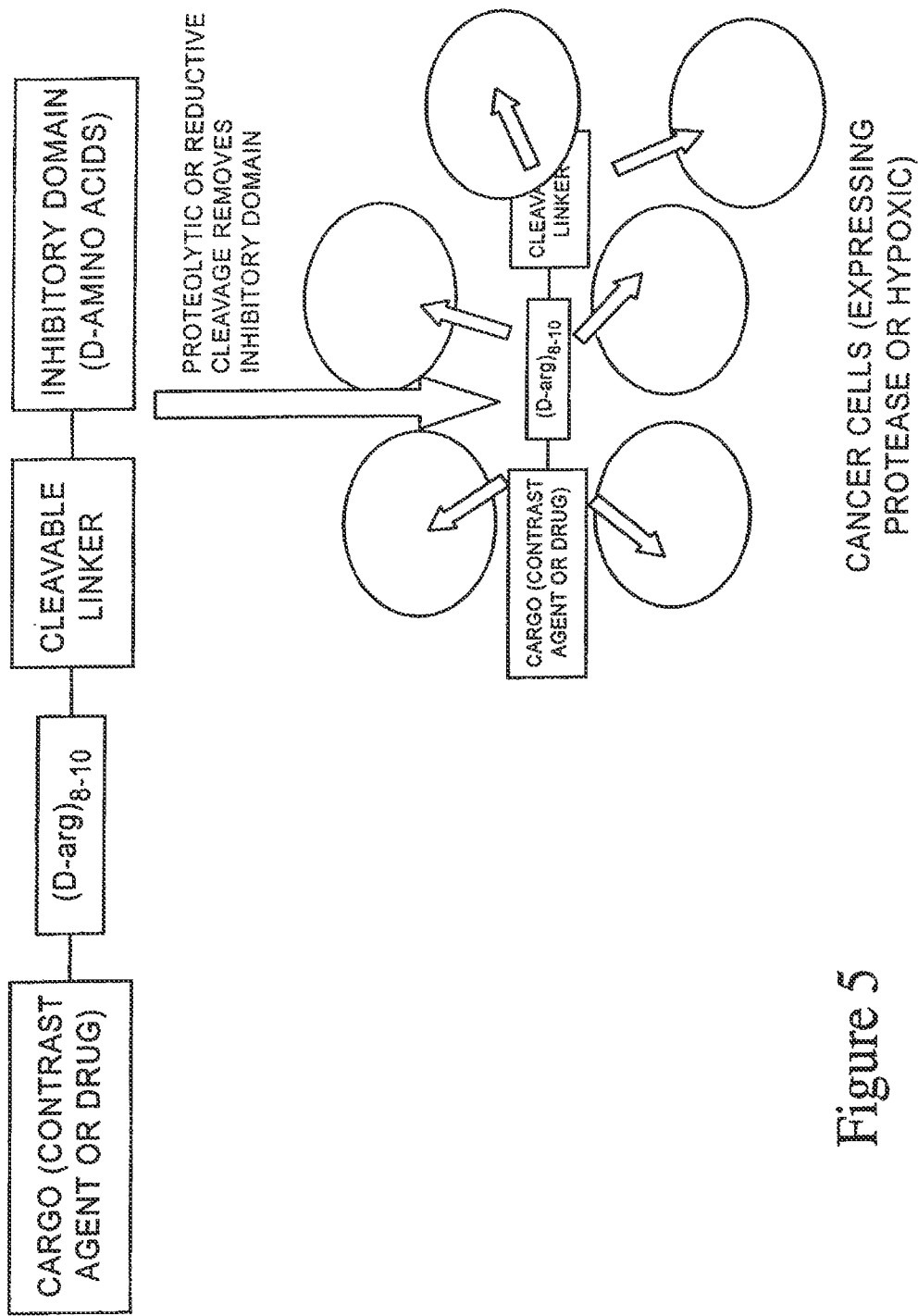
FIG. 5 is a schematic representation of a MTS molecule of FIG. 3 having features of the invention in which the cleavable linker is cleaved by proteolytic enzymes or by the reducing environment found near cancer cells, showing the ability of a molecule of FIG. 3 to facilitate cargo entry into diseased tissue.

However, as illustrated in FIG. 5, the linker portion X may be cleaved, for example, by proteolytic enzymes or reducing environment found near cancerous cells to deliver a marker or a drug to cancerous cells. As shown in FIG. 5, a MTS molecule of FIG. 3 with a cleavable linker X that is cleaved by proteolytic enzymes or by the reducing environment near cancer cells is able to facilitate cargo entry into diseased tissue. Thus, the selective cleavage of the linker X and the resulting separation of cargo C and basic portion B from acidic portion A allows the targeted uptake of cargo into cells having selected features (e.g., enzymes), or located near to, a particular environment. Thus, molecules having features of the invention are able to selectively deliver cargo to target cells without doing so to normal or otherwise non-targeted cells.

In some embodiments, cargo C may be a fluorescent molecule such as fluorescein. Fluorescent cargo moieties enable easy measurement by fluorescence microscopy or flow cytometry in unfixed cultured cells. However, oligoarginine sequences, such as make up portion B, have been demonstrated to import a very wide varieties of cargoes C, ranging from small polar molecules to nanoparticles and vesicles (Tung & Weissleder (2003) Advanced Drug Delivery Reviews 55: 281-294). Thus, in embodiments of the invention, a cargo portion C may be any suitable cargo moiety capable of being taken up by a cell while connected to a basic portion B.

For example, for in vivo imaging purposes, C may be labeled with a positron-emitting isotope (e.g. $^{18}$F) for positron emission tomography (PET), gamma-ray isotope (e.g. $^{99m}$Tc) for single photon emission computed tomography (SPECT), a paramagnetic molecule or nanoparticle (e.g. $Gd^{3+}$ chelate or coated magnetite nanoparticle) for magnetic resonance imaging (MRI), a near infrared fluorophore for near-infra red (near-IR) imaging, a luciferase (firefly, bacterial, or coelenterate) or other luminescent molecule for bioluminescence imaging, or a perfluorocarbon-filled vesicle for ultrasound. For therapeutic purposes, for example, suitable classes of cargo include but are not limited to: a) chemotherapeutic agents such as doxorubicin, mitomycin, paclitaxel, nitrogen mustards, etoposide, camptothecin, 5-fluorouracil, etc.; b) radiation sensitizing agents such as porphyrins for photodynamic therapy, or $^{10}$B clusters or $^{157}$Gd for neutron capture therapy; or c) peptides or proteins that modulate apoptosis, the cell cycle, or other crucial signaling cascades. Existing chemotherapeutic drugs may be used, although they may not be ideal, because they have already been selected for some ability to enter cells on their own. In embodiments of the molecules of the invention, cargoes that are unable to enter or leave cells without the help of the polybasic portion B may be preferred.

Cargo C may include a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, radioactive isotopes of Lu, and others.

Cargo portion C may include a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720, U.S. Pat. No. 5,227,487, and U.S. Pat. No. 5,543,295.

A cargo portion C may include a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356. A cargo portion C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. No. 6,080,852, U.S. Pat. No. 6,025,505, U.S. Pat. No. 5,936,087, U.S. Pat. No. 5,750,409. A cargo portion C may include a cyanine dye, such as, for example, Cy3, Cy3B, Cy3.5, Cy5, Cy5.5, Cy 7.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and may be, or may be included in, a cargo portion C. A cargo portion C may also be or include a fluorescence quencher, such as, for example, a (4-dimethylamino-phenylazo)benzoic acid (DABCYL) group.

Figure 2F:
FIG. 2F is a schematic representation of a MTS molecule having features of the invention comprising a fluorescent cargo portion C, a basic portion B, a linker region X, and an acidic portion A having a quencher Q attached.

A pair of compounds may be connected to form a molecular beacon, having complementary regions with a fluorophore and a fluorescent quencher associated together so that the fluorescence of the fluorophore is quenched by the quencher. One or both of the complementary regions may be part of the cargo portion C. Where only one of the complementary regions (e.g., the fluorescent moiety) is part of the cargo portion C, and where the quencher moiety is part of the linker X or the acidic portion A, then cleavage of the linker X will allow fluorescence of the fluorescent portion and detection of the cleavage. Upon cellular uptake, the fluorescent portion of a molecular beacon will allow detection of the cell. For example, as illustrated in FIG. 2F, a quencher Q may be attached to an acidic portion A to form a MTS molecule having features of the invention Q-A-X-B-C where cargo C is fluorescent and is quenched by Q. The quenching of C by Q is relieved upon cleavage of X, allowing fluorescent marking of a cell taking up portion B-C. The combination of fluorescence dequenching and selective uptake should increase contrast between tissues able to cleave X compared to those that cannot cleave X.

Cargo C may include a chemotherapeutic moiety, such as a chemical compound useful in the treatment of cancer, or other therapeutic moiety, such as an agent useful in the treatment of ischemic tissue, or of necrotic tissue, or other therapeutic agent.

MTS molecules having features of the invention may be synthesized by standard synthetic techniques, such as, for example, solid phase synthesis including solid phase peptide synthesis. An example of peptide synthesis using Fmoc is given as Example 1 below. For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1M acetic acid solution and lyophilized. The peptide can be isolated by an initial separation by gel filtration, to remove peptide dimers and higher molecular weight polymers, and also to remove undesired salts. The partially purified peptide may be further purified by preparative HPLC chromatography, and the purity and identity of the peptide confirmed by amino acid composition analysis, mass spectrometry and by analytical HPLC (e.g., in two different solvent systems).

The invention also provides polynucleotides encoding MTS molecules described herein. The term "polynucleotide" refers to a polymeric form of nucleotides of at least 10 bases in length. The nucleotides can be ribonucleotides, deoxynucleotides, or modified forms of either type of nucleotide. The term includes single and double stranded forms of DNA. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

These polynucleotides include DNA, cDNA, and RNA sequences which encode MTS molecules having features of the invention, or portions thereof. Peptide portions may be produced by recombinant means, including synthesis by polynucleotides encoding the desired amino acid sequence. Such polynucleotides may also include promoter and other sequences, and may be incorporated into a vector for transfection (which may be stable or transient) in a host cell.

The construction of expression vectors and the expression of genes in transfected cells involves the use of molecular cloning techniques that are well known in the art. See, for example, Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., most recent Supplement). Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences. As used herein, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989). Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Guzman ed., 1982). Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

It will be understood that the compounds of the present invention can be formulated in pharmaceutically useful compositions. Such pharmaceutical compositions may be prepared according to known methods. For example, MTS compounds having features of the invention, and having a cargo portion C that is, for example, a therapeutic moiety, may be combined in admixture with a pharmaceutically acceptable carrier vehicle. Suitable vehicles and their formulation, inclusive of other human proteins, e.g. human serum albumin are described, for example, in *Remington's Pharmaceutical Sciences* by E. W. Martin, which is hereby incorporated by reference. Such compositions will contain an effective amount of the compounds hereof together with a suitable amount of vehicle in order to prepare pharmaceutically acceptable compositions suitable for effective administration. Dosages and dosing regimens may be determined for the indications and compounds by methods known in the art, including determining (e.g., in experimental animals) the effective dose which causes half of those treated to respond to the treatment ($ED_{50}$) by providing a range of doses to experimental animals or subjects and noting the responses.

Example 1

Peptide Synthesis

A number of peptides whose cell uptake could be modulated were synthesized. In the following, the following symbols, where used, are used with the indicated meanings: Fl=fluorescein; aca=aminocaproic acid linker (—HN—$(CH_2)_5$—CO—), C=L-cysteine, E=L-glutamate, R=L-arginine, D=L-aspartate, K=L-lysine, A=L-alanine, r=D-arginine, c=D-cysteine, e=D-glutamate, P=L-proline, L=L-leucine, U=glycine, V=valine, I=isoleucine, M=methionine, F=phenylalanine, Y=tyrosine, W=tryptophan, H=histidine, Q=glutamine, N=asparagine, S=serine, and T=threonine. In sequences discussed below, lower case letters indicate the D isomer of the amino acid.

Peptides were synthesized on a peptide synthesizer (Pioneer Peptide Synthesis System by Applied Biosystems) using solid phase synthesis method and commercial available Fmoc amino acids, resins, and the other reagents. The peptides were cleaved with TFA/thioanisole/triisopropylsilane or TFA/thioanisole/triisopropylsilane/ethanedithiol. Peptides were labeled with 5- (and -6)carboxyfluorescein succinimidyl ester on the amino group on the peptide or with 5-iodoacetamidofluorescein on the thiol group on the peptide. The crude peptide was purified on HPLC and lyophilized overnight. Each peptide composition was confirmed by mass spectrometry.

Example 2

Peptide Cleavage by Enterokinase

10 µl 0.38 mM peptide dissolved in water stock solution was added to 10 µl 1 U/µl Enterokinase (Invitrogen, EKmax) and the cleavage progress was monitored by injecting 5 µl of the reaction mixture on HPLC monitored at 440 nm. The peptide was designed to be a substrate for enterokinase, with cleavage by enterokinase expected between the K and A residues. A High Performance Liquid Chromatography (HPLC) chromatogram of the peptide EDDDDKA-aca-$R_9$-aca-C(Fl)-$CONH_2$ (SEQ ID NO: 3) (before cleavage of linker portion between K and A) is illustrated in FIG. 6A. (The term "$R_9$" indicates a sequence of nine arginines; SEQ ID NO:47.) The HPLC chromatograms showed that the peptide was cleaved almost completely after 15 min reaction time. FIG. 6B illustrates the HPLC chromatogram of the peptide of FIG. 6A after cleavage by enterokinase. The new peak was collected and determined on a mass spectrometer. The determined mass corresponded (as expected) to cleavage between K and A in the sequence of EDDDDKA-aca-$R_9$-aca-C(Fl)-$CONH_2$ (SEQ ID NO: 3).

Example 3

Peptides Having Acidic Portions to Veto Uptake

Peptide molecules having features of the invention, having fluorescent cargo moieties connected to basic portions (having multiple arginine residues), these latter being linked by cleavable linkers to an acidic portion (having multiple glutamate residues), were synthesized and tested for ability to deliver cargo into cells. Peptides showing ability of oligoglutamates to veto oligoarginine-mediated cellular uptake include:

```
                                              (SEQ ID NO: 5)
Fl-aca-CRRRRRRRRR-aca-EEEEEEEEEC-CONH2
(linear or cyclic, 5-47)

(SEQ ID NO: 6)
Fl-aca-CEEEE-aca-RRRRRRRRRC-CONH2
(linear or cyclic, 6-10)
```

Peptides showing cleavage-dependent uptake include:

H₂N-EEEEEDDDDKA-aca-RRRRRRRRR-aca-C(Fl)-CONH₂ (SEQ ID NO: 7)
(6-14, Enterokinase substrate, cleaved after
DDDDK; SEQ ID NO: 56)

H₂N-EDDDDKA-aca-RRRRRRRRR-aca-C(Fl)-CONH₂ (SEQ ID NO: 8)
(6-16, Enterokinase substrate)

H₂N-EEEEEDDDDKARRRRRRRRR-aca-C(Fl)-CONH₂ (SEQ ID NO: 9)
(6-27, Enterokinase substrate)

H₂N-EEDDDDKA-aca-rrrrrrrrr-aca-C(Fl)-CONH₂
(6-29, Enterokinase substrate)

H₂N-DDDDDDKARRRRRRRRR-aca-C(Fl)-CONH₂ (SEQ ID NO: 11)
(7-2, Enterokinase substrate)

H₂N-EEDDDDKAR-aca-RR-aca-RR-aca-RR-aca-RR- (SEQ ID NO: 12)
aca-C(Fl)-CONH₂
(7-4, Enterokinase substrate)

H₂N-eeeeee-aca-PLGLAG-rrrrrrrrr-aca-c(Fl)-CONH₂
(7-6, MMP-2 substrate, cleaved between PLG
and LAG)

Example 4

Peptide Cleaved by Matrix Metalloproteinase-2 (MMP-2)

Figure 7A:
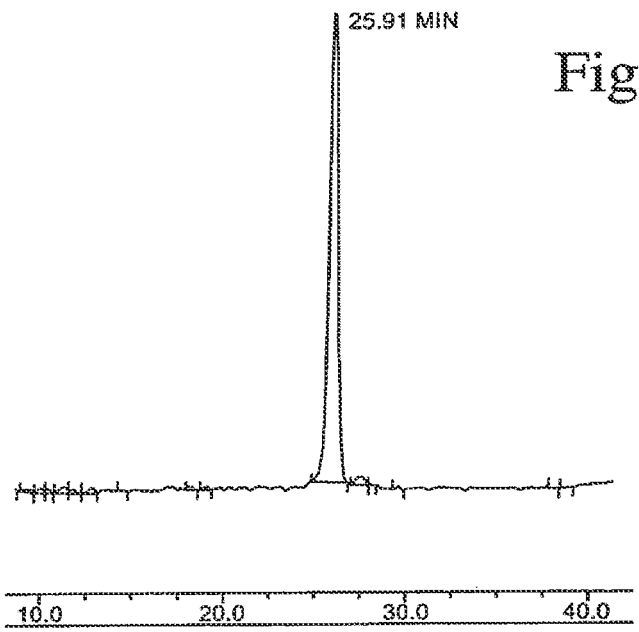
FIG. 7A illustrates a HPLC chromatogram of a peptide having features of the invention before cleavage of linker portion X that is a substrate for matrix metalloproteinase-2 (MMP-2).
Figure 7B:
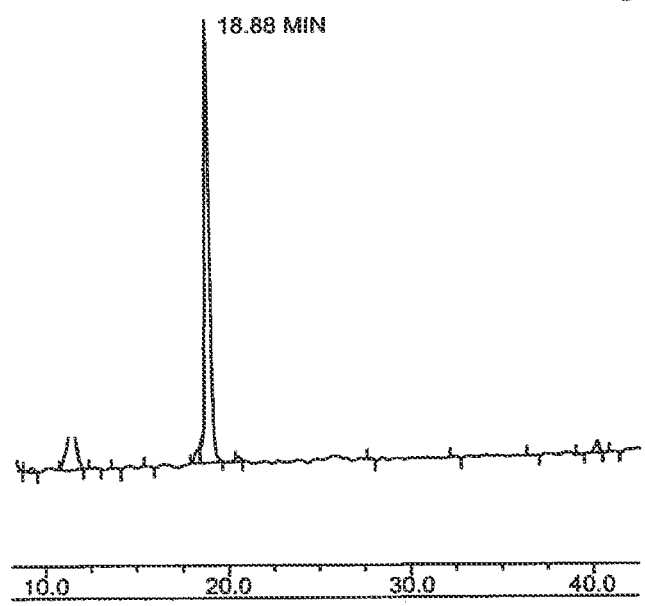
FIG. 7B illustrates a HPLC chromatogram of the peptide of FIG. 7A after cleavage of linker portion X by MMP-2.

MMP-2 (5 μg in 88 μl) was activated from human rheumatoid synovial fibroblast proenzyme (Invitrogen) in Tris-HCl buffer as described by Stricklin et al (1983) *Biochemistry* 22: 61 and Marcy et al (1991) *Biochemistry* 30: 6476), then incubated with 32 μl 0.5 mM peptide stock solution for one hour at room temperature. FIG. 7A illustrates a HPLC chromatogram of the substrate peptide before cleavage by MMP-2. Enzyme cleavage progress was monitored by HPLC at 215 nm absorbance. FIG. 7B is a HPLC chromatogram of the peptide after cleavage by MMP-2, showing complete conversion to a new species.

Example 5

FACS Analysis of Cell Uptake

The human T cell line-wide type Jurkat cells were cultured in RPMI 1640 media with 10% (v/v) deactivated fetal calf serum (FBS) and reached density ~1×10⁶ cells/ml. The media was refreshed one day before being used. Before the experiment, the Jurkat cells were washed with HESS buffer three times and resuspended in HBSS at (0.5-1)×10⁶ cells/ml density. In the cell uptake experiment, cells were stained with 1 μM peptide or compound at room temperature for 10 min, then washed twice with cold HESS and submitted for FACS analysis. Cell uptake was monitored by fluorescence at 530 nm run on FACS and 5,000-10,000 events were recorded from cells judged to be healthy by their forward and side scatter. The data represent mean fluorescence of the recorded cell population indicating uptake of the fluorescently labeled compounds. In most experiments, Fl-GGR₁₀-CONH₂ (abbreviated as "R10" on the graphs; SEQ ID NO: 49) was included as a positive control for uptake.

Figure 8:
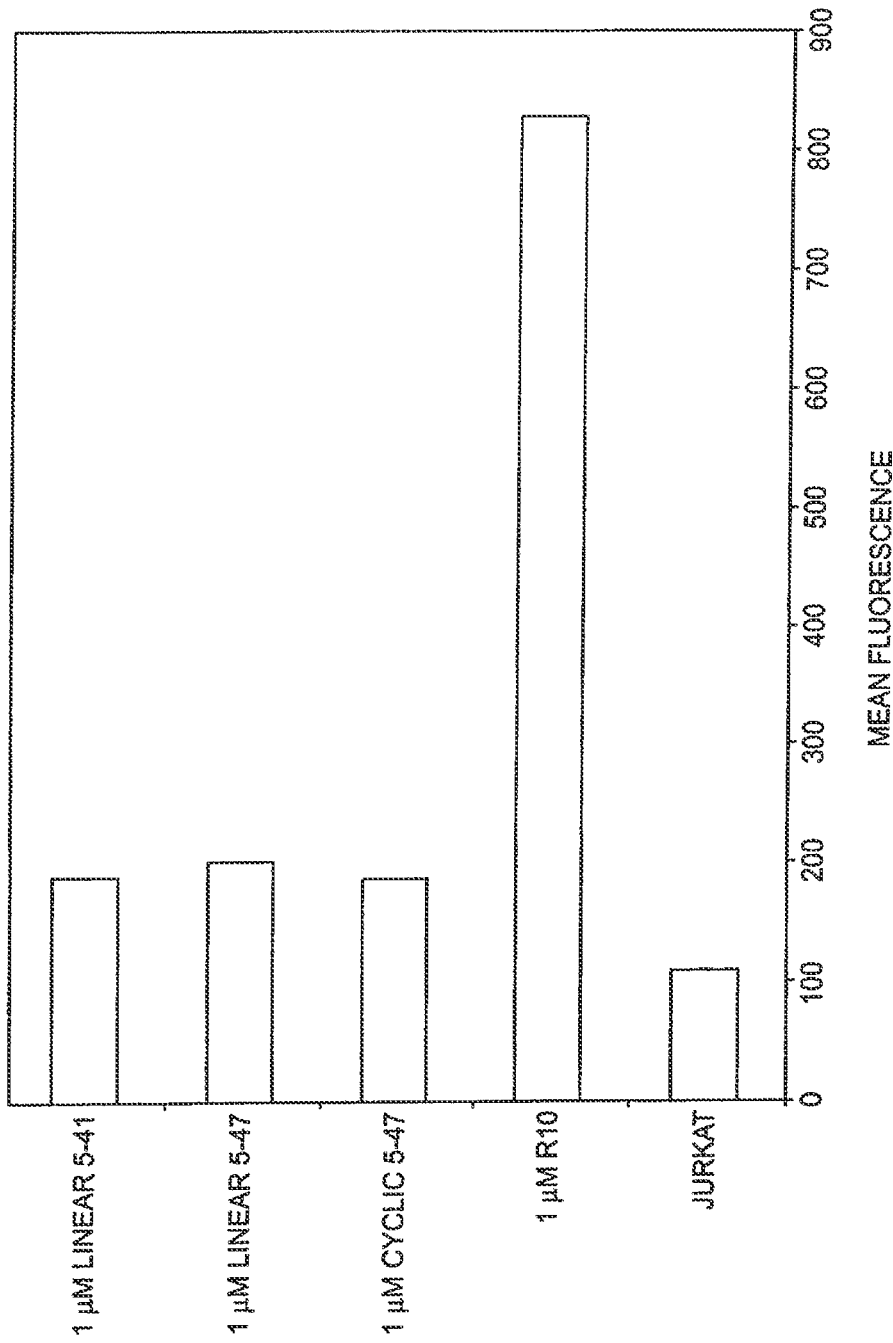
FIG. 8 illustrates the mean fluorescence measured by Fluorescence-Activated Cell Sorter (FACS) analysis of Jurkat cell populations incubated for ten minutes with MTS molecules having features of the invention, with fluorescent cargo moieties.
Figure 9:
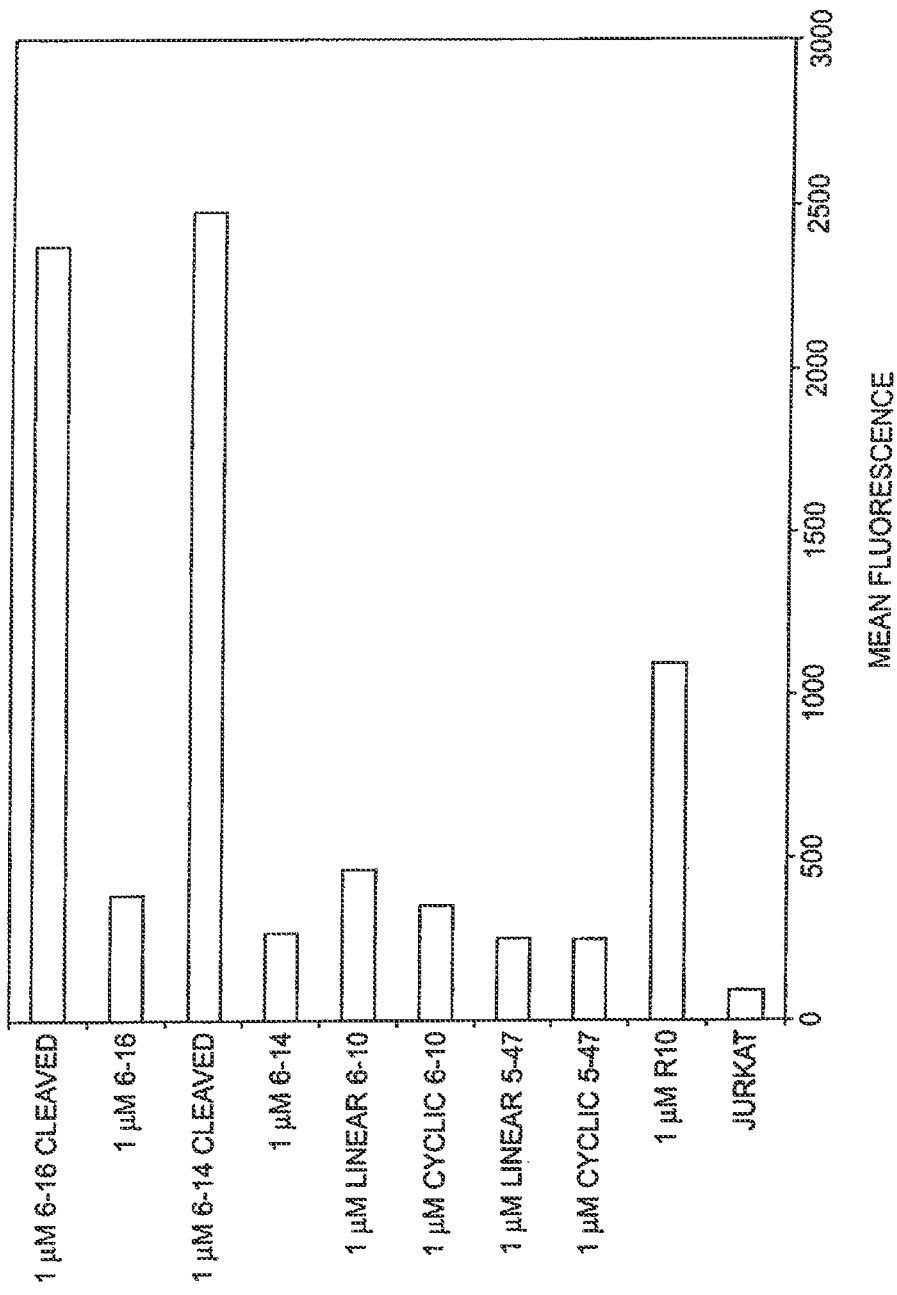
FIG. 9 illustrates the mean fluorescence measured by FACS analysis of Jurkat cell populations incubated for ten minutes with MTS molecules having features of the invention, with fluorescent cargo moieties.
Figure 10:
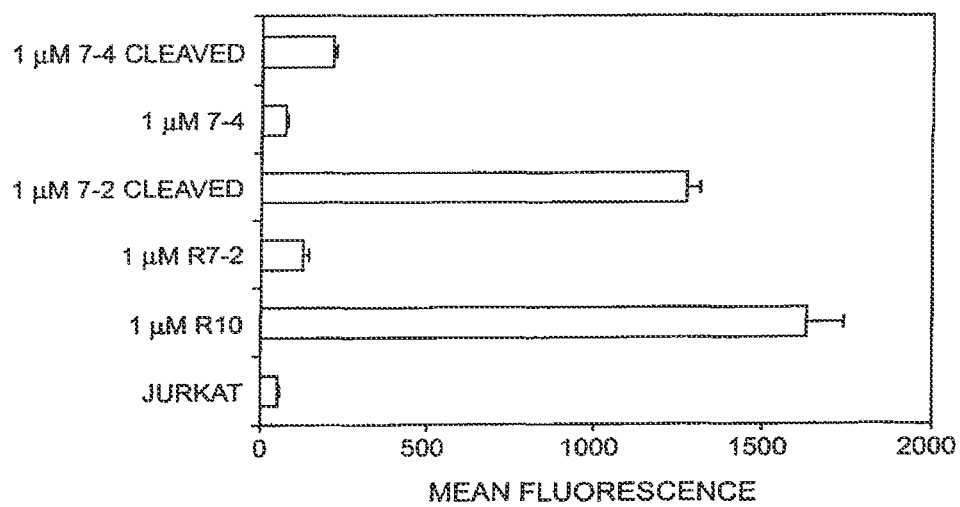
FIG. 10 illustrates the mean fluorescence measured by FACS analysis of Jurkat cell populations incubated for ten minutes with MTS molecules having features of the invention, with fluorescent cargo moieties.

The mean fluorescence measured in Jurkat cells incubated for ten minutes with the indicated peptides (each with fluorescent cargo moieties) is shown in FIGS. 8, 9 and 10.

As shown in FIG. 9, compounds 6-14 (SEQ ID NO: 7) and 6-16 (SEQ ID NO: 8) showed greatly enhanced fluorescence, indicating much greater uptake, of the cleaved form of the peptides than the intact peptides. Similarly, as shown in FIG. 10, compounds 7-2 (SEQ ID NO: 11) and 7-6 also showed greatly enhanced fluorescence after cleavage compared with the fluorescence of the uncleaved compounds. Thus, these results demonstrate prevention of cellular uptake of compounds having basic amino acids by linkage to an acidic portion. Additionally, these results demonstrate enhanced cellular uptake of fluorescent portions of these peptides (having basic amino acids) following cleavage of the acidic portions.

Figure 11:
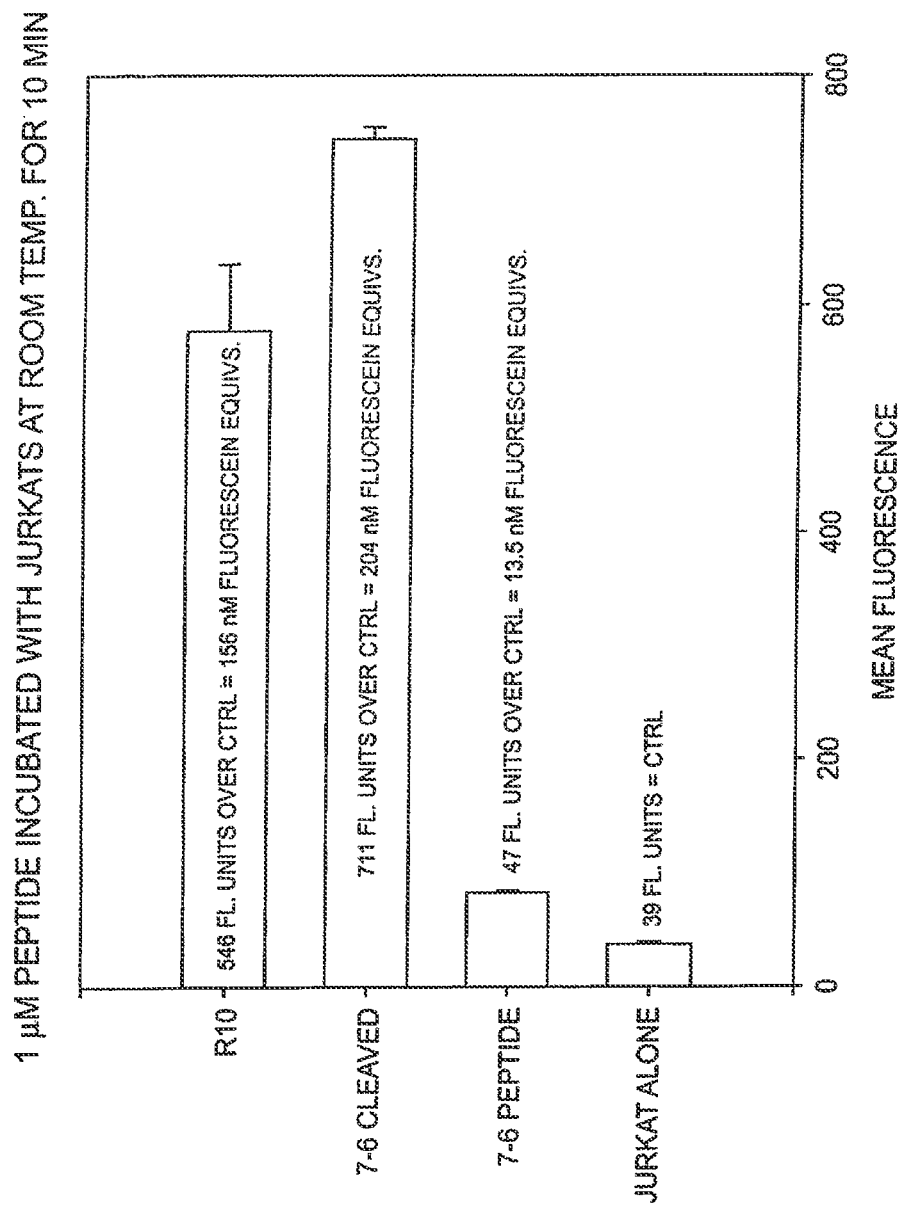
FIG. 11 illustrates the mean fluorescence measured by FACS analysis of Jurkat cell populations incubated for ten minutes with MTS molecules having features of the invention, with fluorescent cargo moieties.
Figure 12:
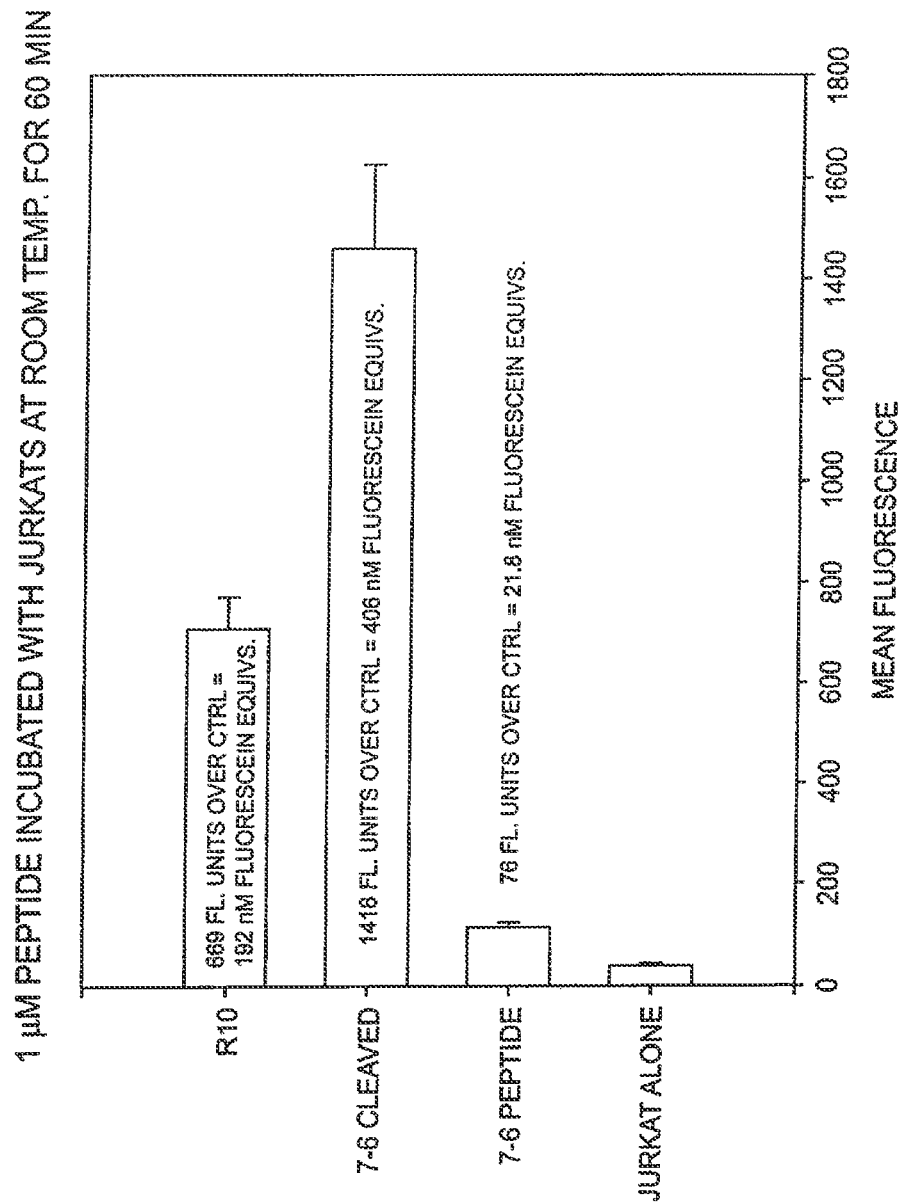
FIG. 12 illustrates the mean fluorescence measured in Jurkat cells incubated for one hour with the MTS molecules of FIG. 11.

Such Cellular uptake increases as incubation time increases. FIG. 11 illustrates the mean fluorescence measured in Jurkat cells incubated for ten minutes with the indicated peptides having fluorescent cargo moieties, basic and acidic portions, and cleavable linker portions. As shown in FIG. 12, the mean fluorescence measured in Jurkat cells incubated for one hour was increased compared to the fluorescence measured as shown in FIG. 11.

The ability of MTS molecules having disulfide linkers X to provide controlled delivery of a cargo portion was tested using peptide 7-45 having the structure

Figure 13:
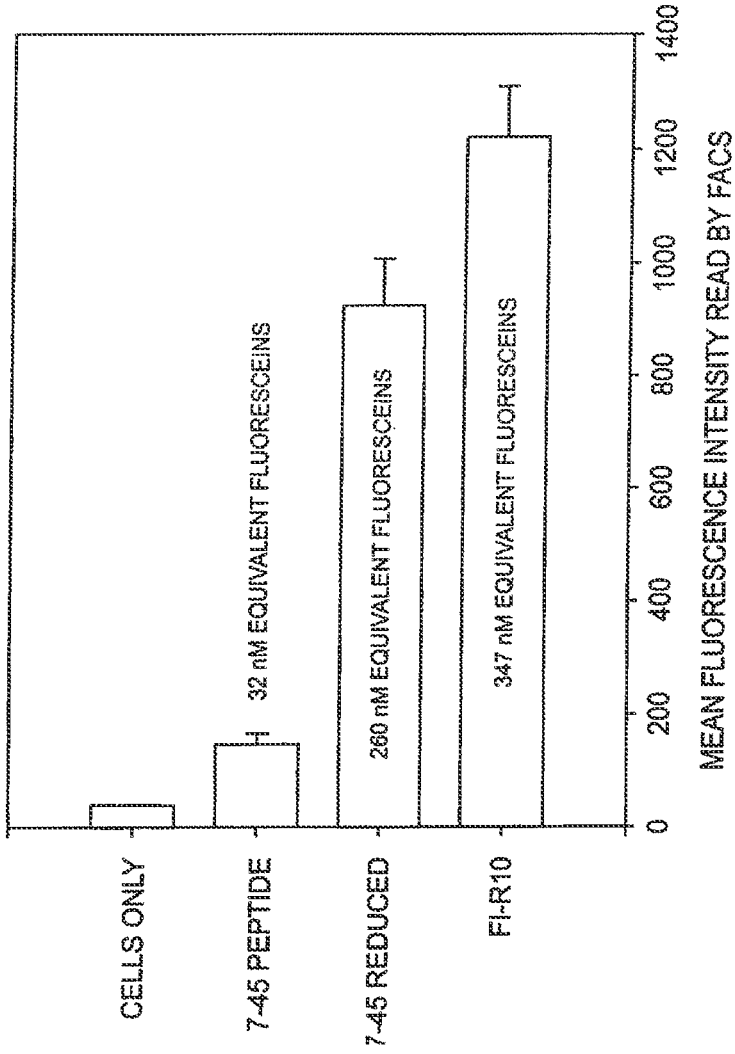
FIG. 13 illustrates the mean fluorescence measured in Jurkat cells incubated for ten minutes with MTS molecules having a disulfide linker connecting an acidic portion with a fluorescently labeled basic portion, or with the fluorescently labeled basic portion alone.
Figure 14A:
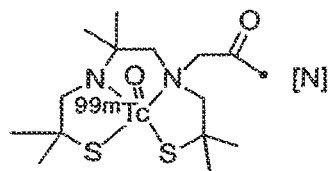
FIG. 14 illustrates some moieties suitable as part or all of a cargo portion of an MTS molecules having features of the invention.
Figure 14D:
Figure 14B:
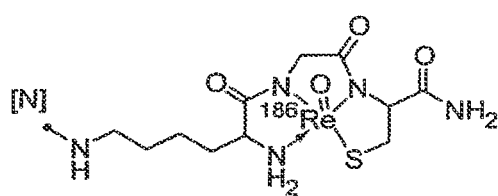
Figure 14E:
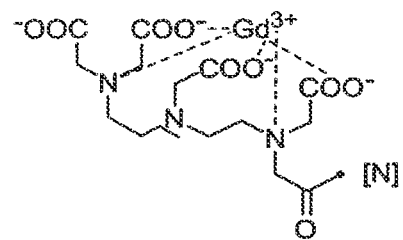
Figure 14C:
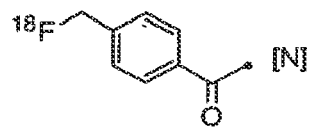
Figure 14F:
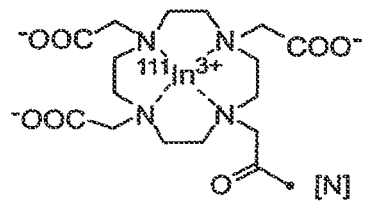
Figure 14G:
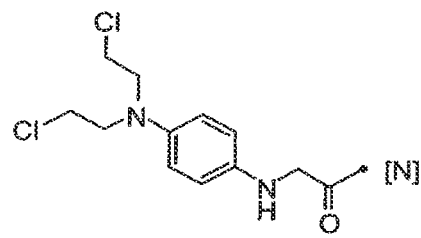
Figure 14H:
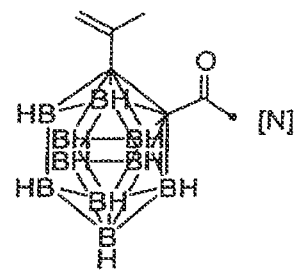
Figure 14I:
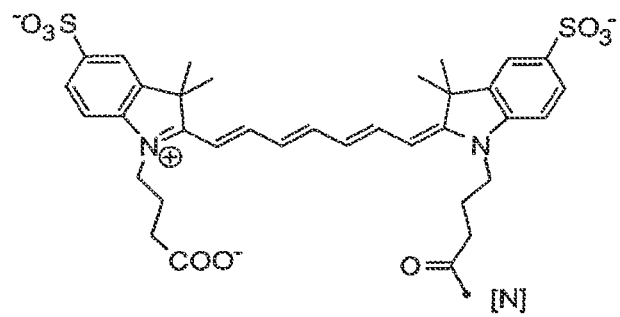
Figure 14J:
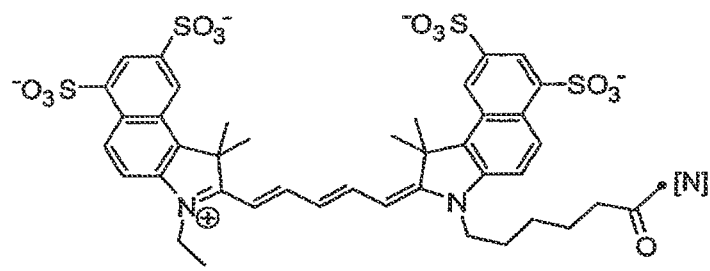
Figure 14K:
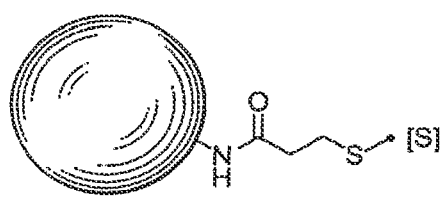
Figure 14L:
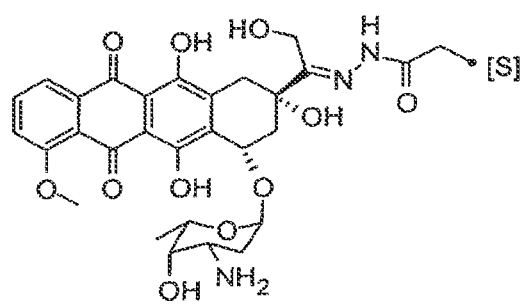
Figure 14M:
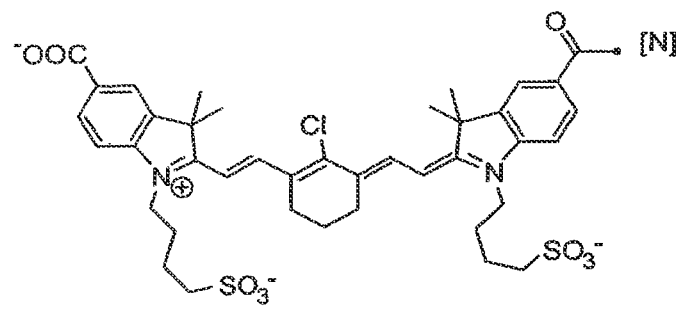
Figure 14N:
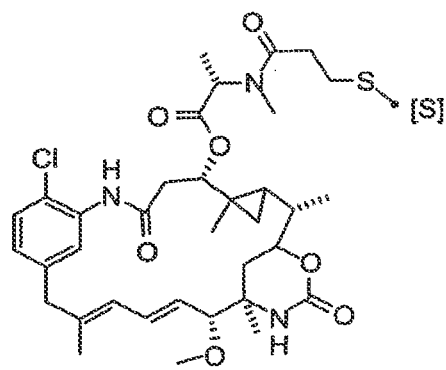
Figure 15A:
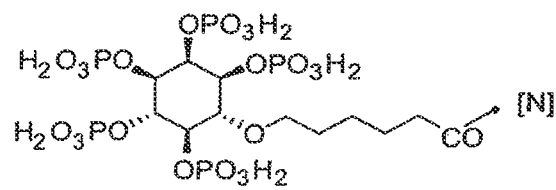
FIG. 15 illustrates some moieties suitable for use as part or all of an acidic portion A.
FIG. 15d=SEQ ID NO:51.
FIG. 15e=SEQ ID NO:52.
FIG. 15f=SEQ ID NO:53.
Figure 15B:
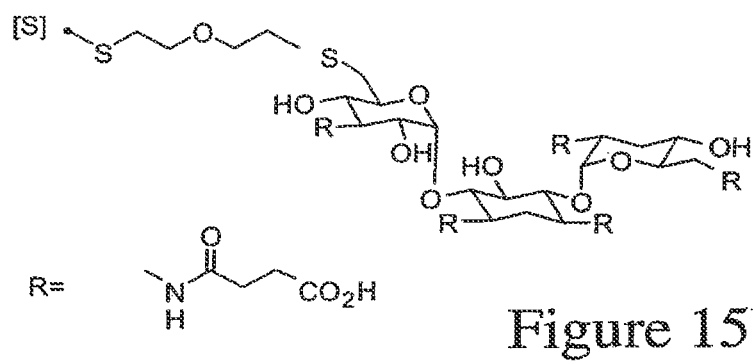
Figure 15C:
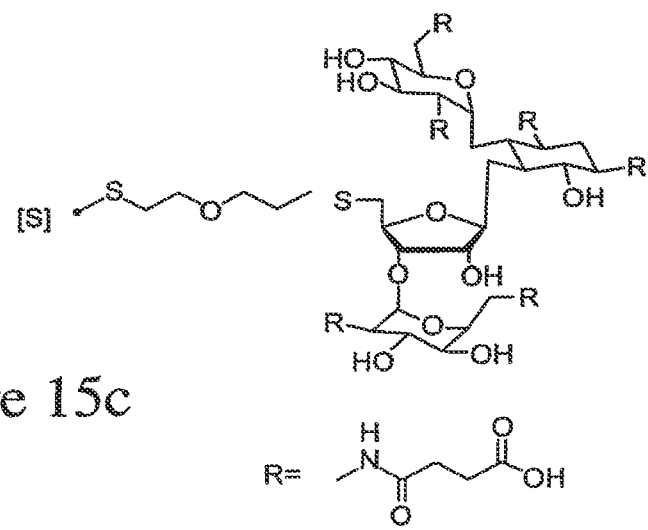
Figure 15D:
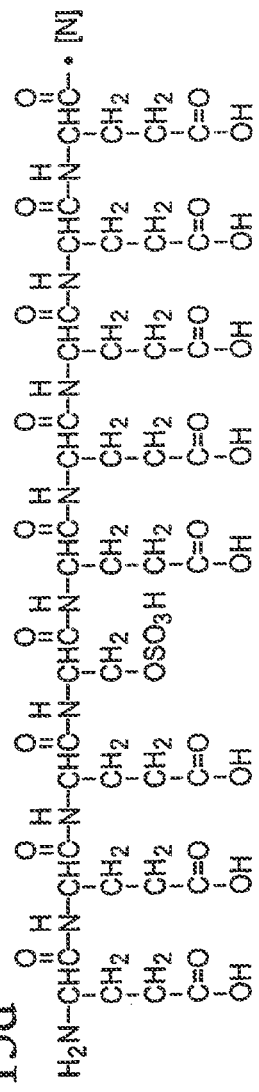
Figure 15E:
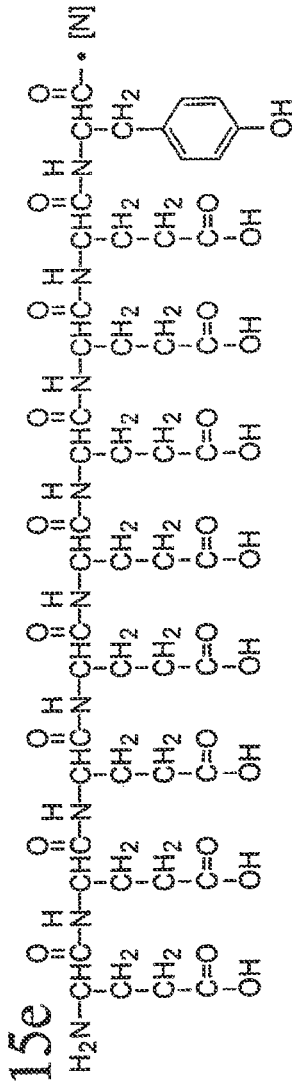
Figure 15F:
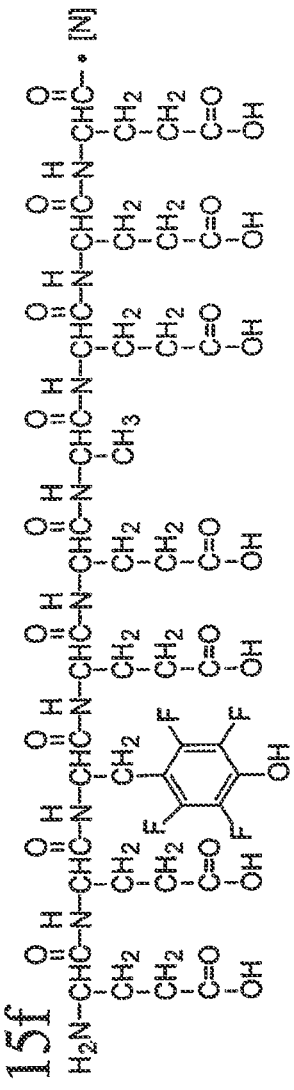
Figure 15G:
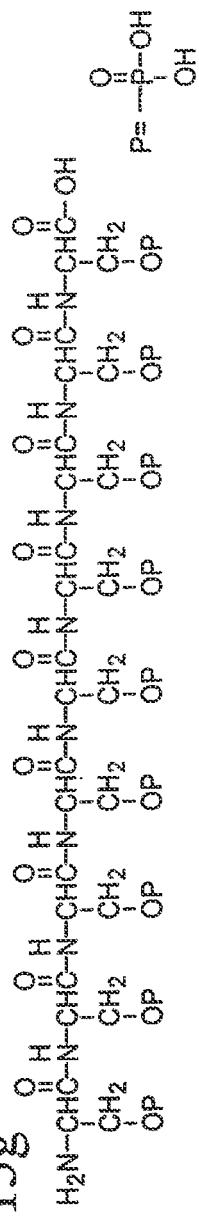
Figure 15H:
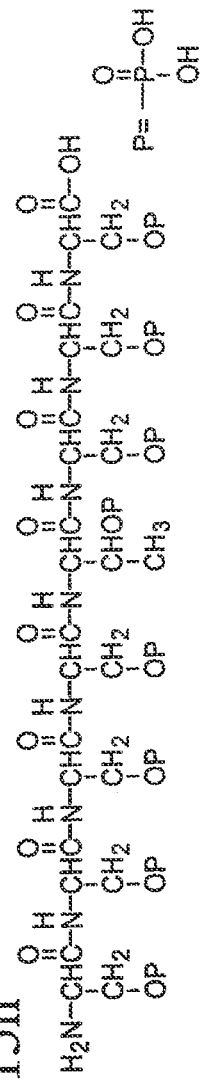
Figure 15I:
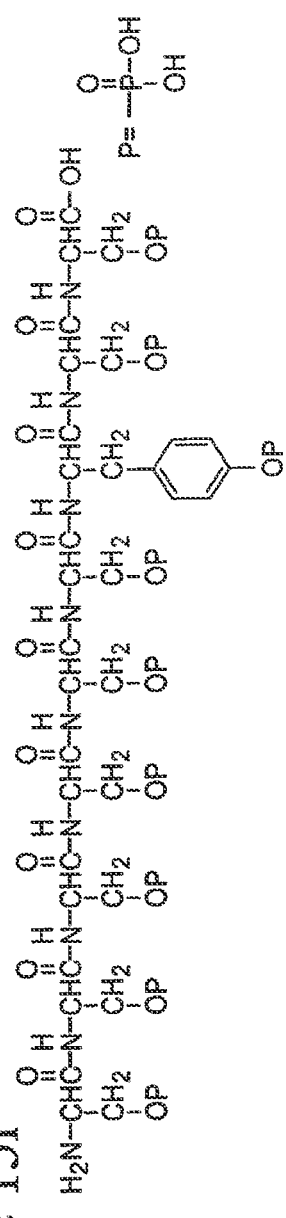
Figure 15J:
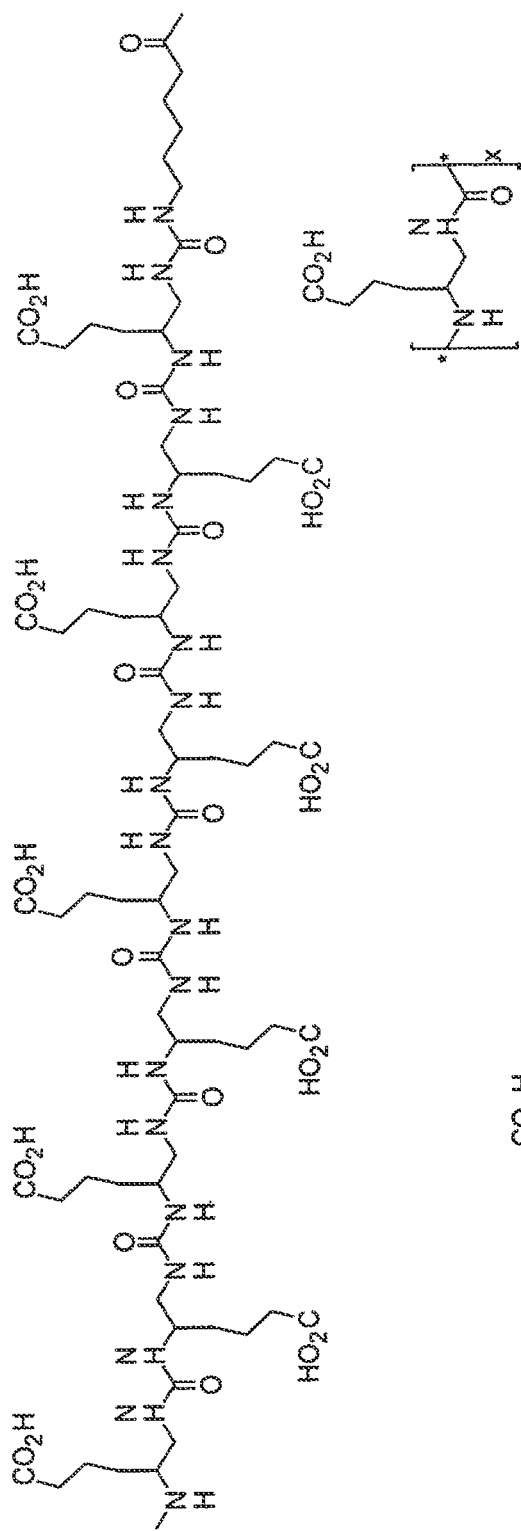
Figure 15K:
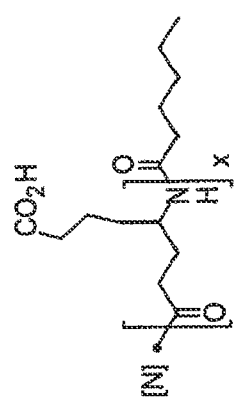
Figure 15L:
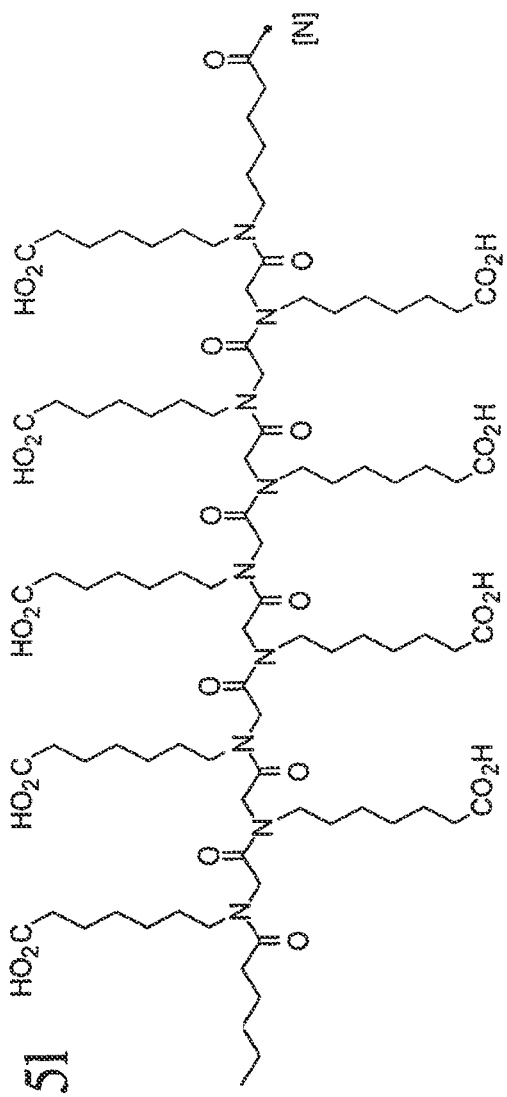
Figure 15M:
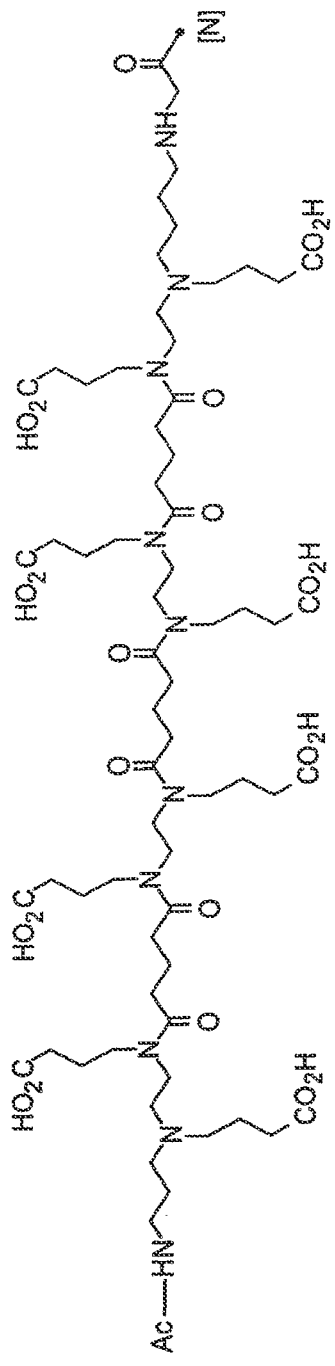
Figure 15N:
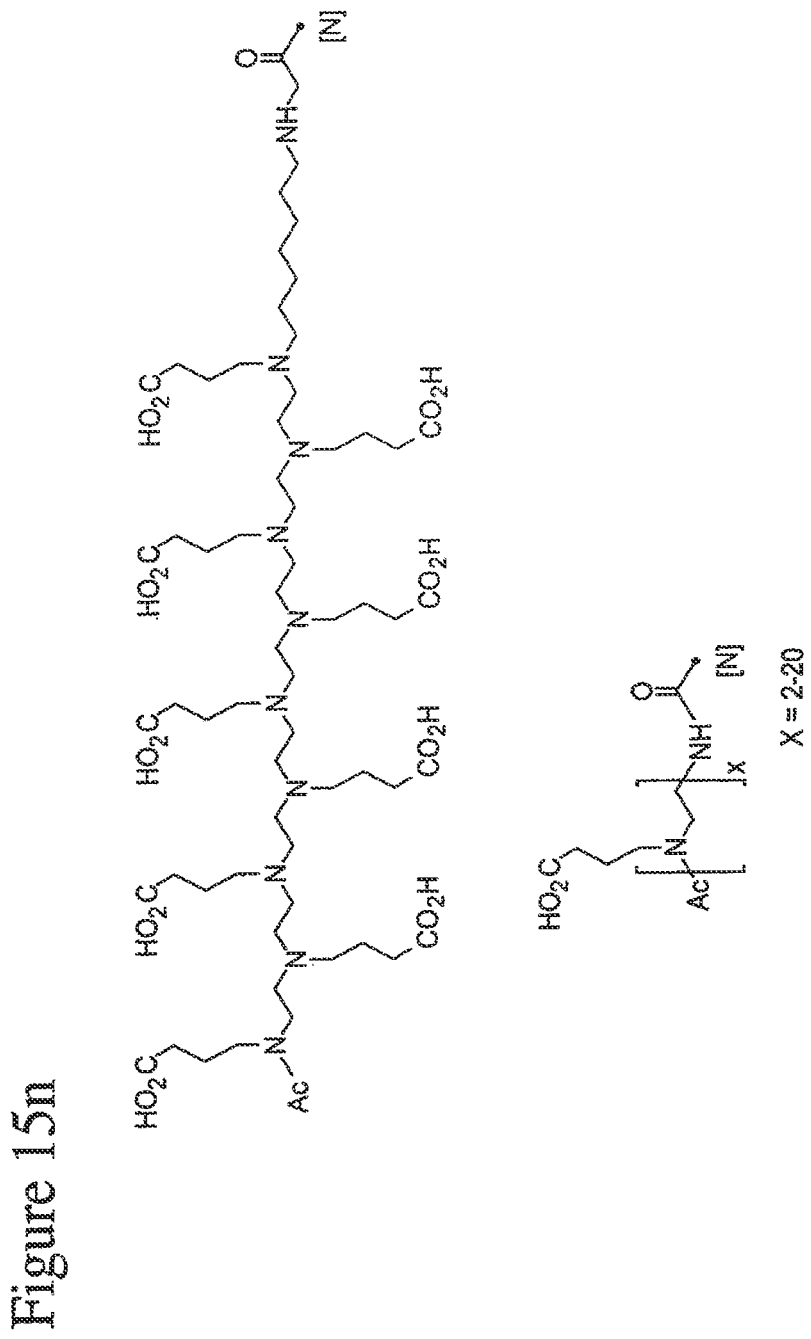
Figure 15O:
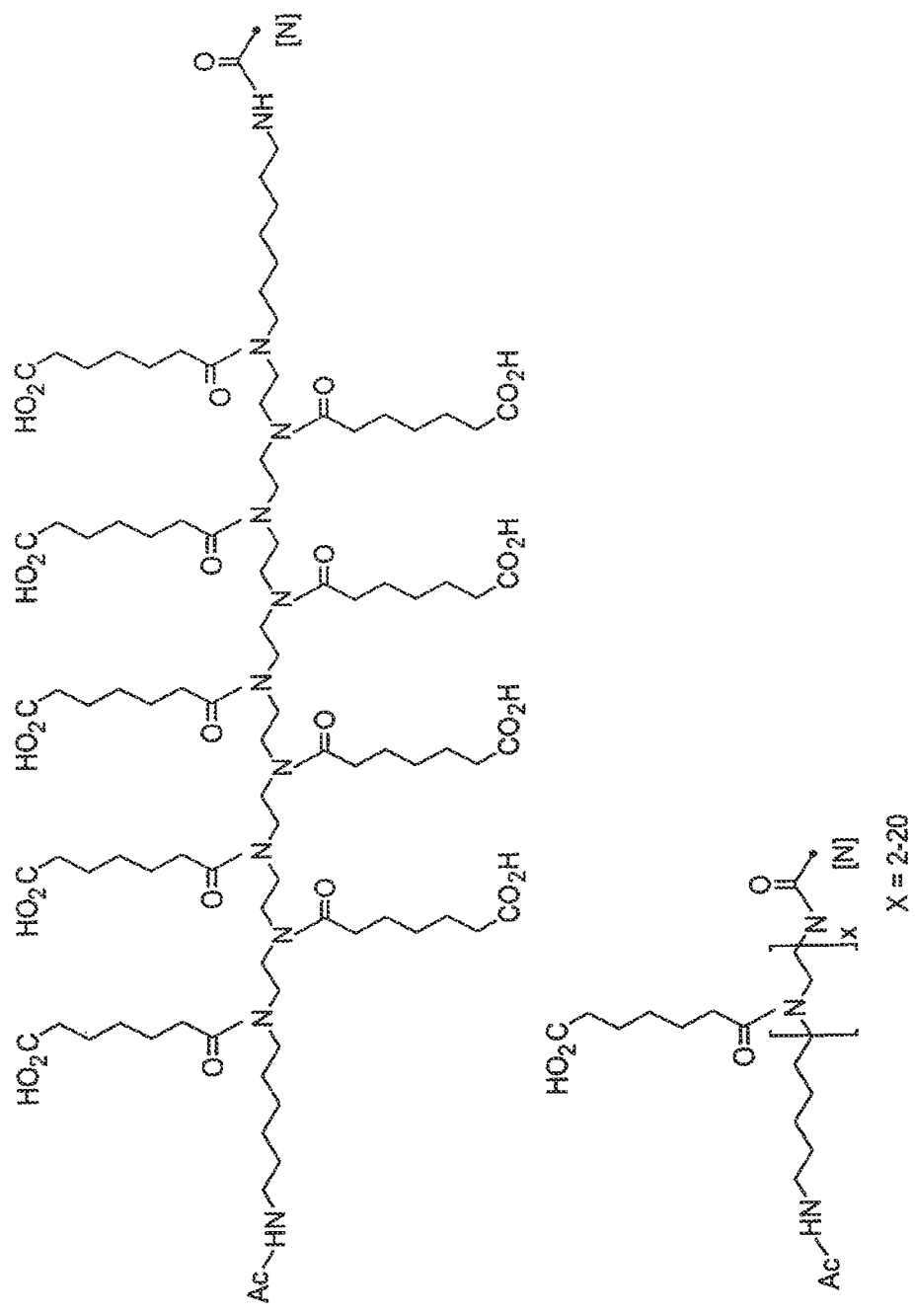
Figure 15P:
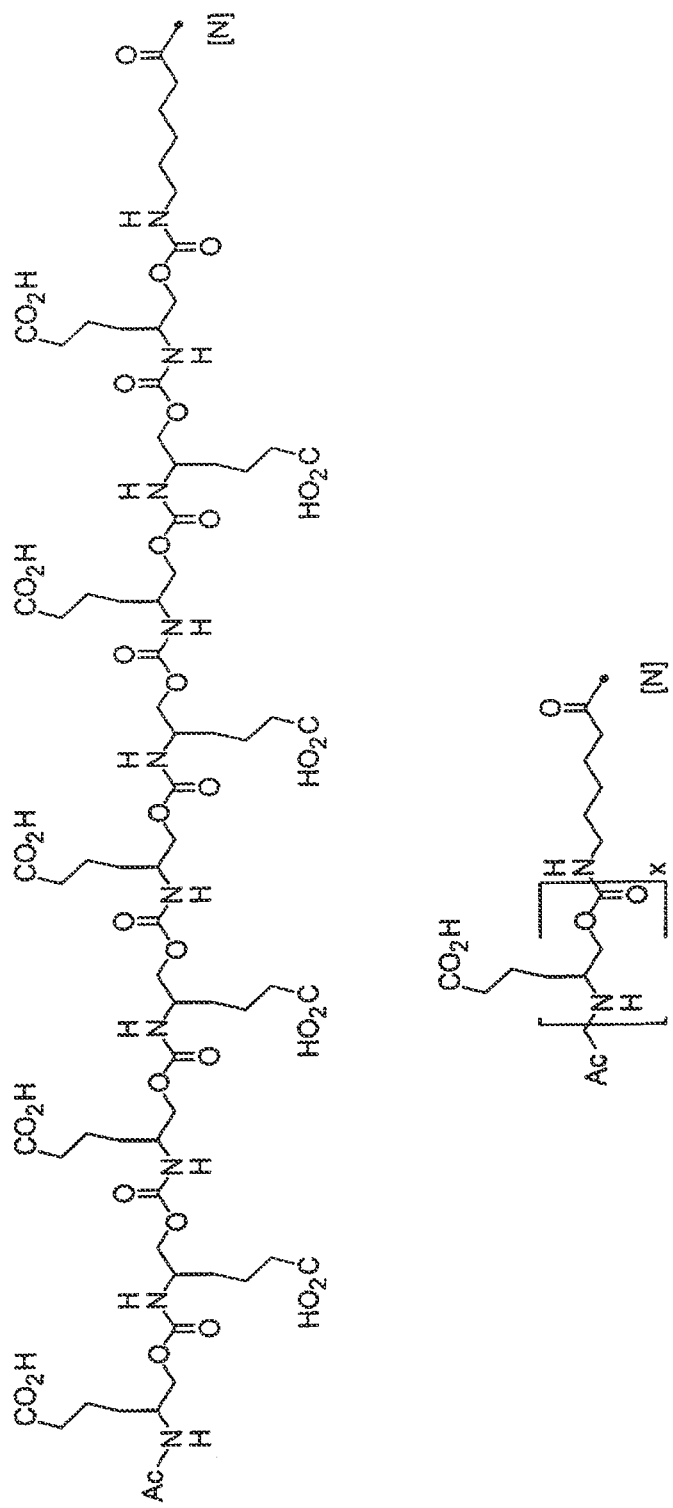
Figure 15Q:
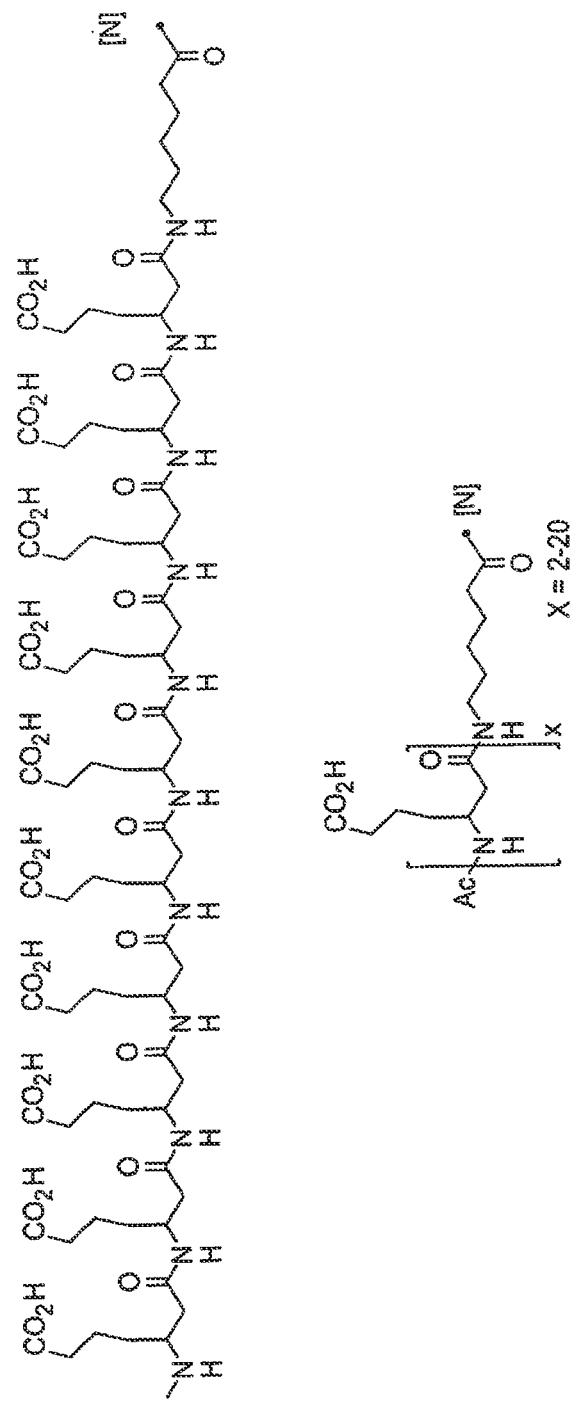
Figure 15R:
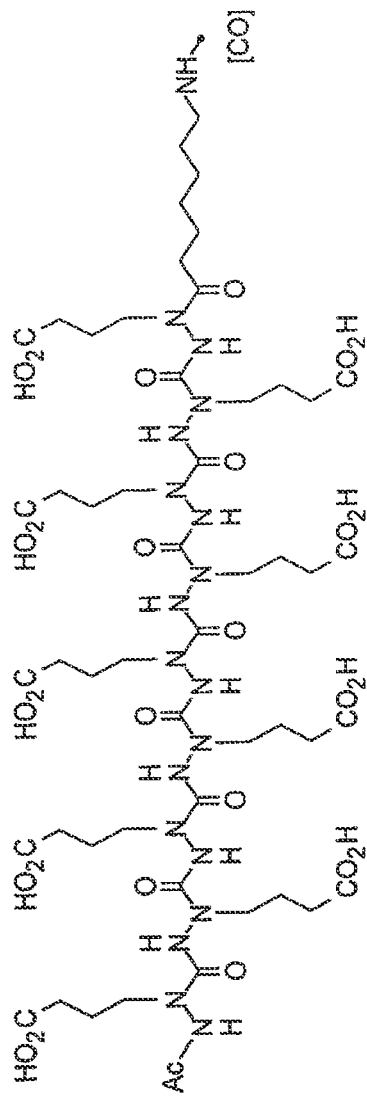
Figure 15S:
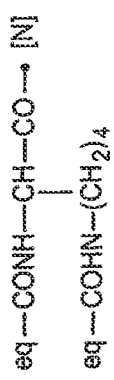
Figure 16A:
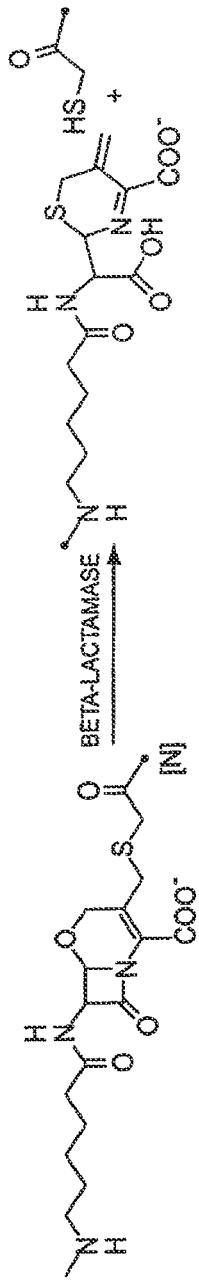
FIG. 16 illustrates some moieties suitable for use as part or all of a linker X.
Figure 16B:
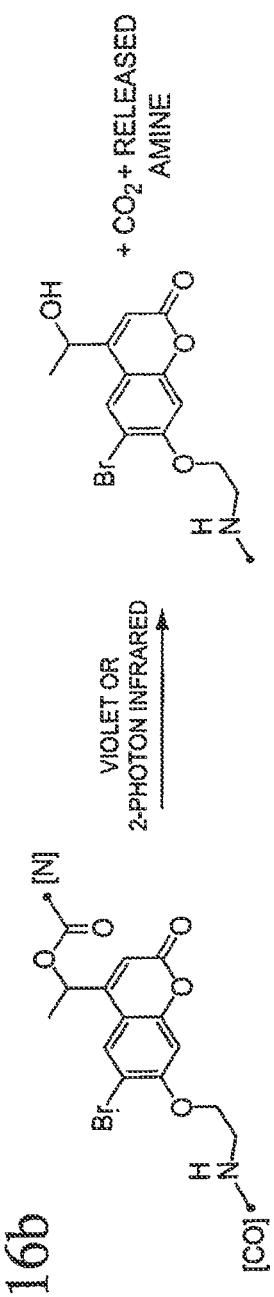
Figure 16C:
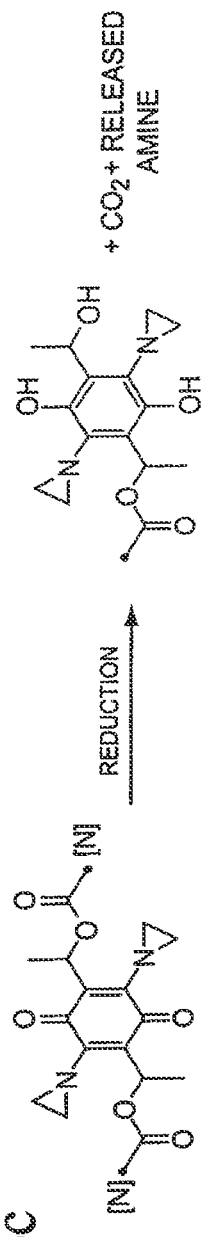
Figure 16D:
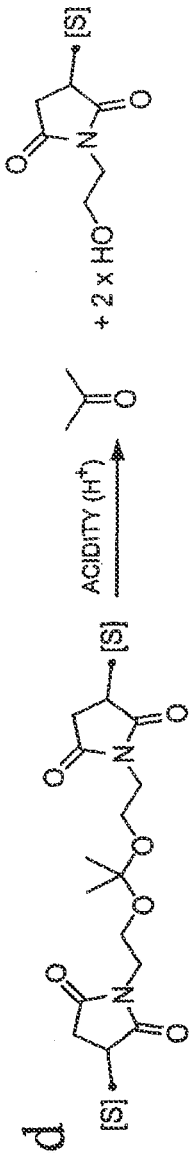
Figure 16E:
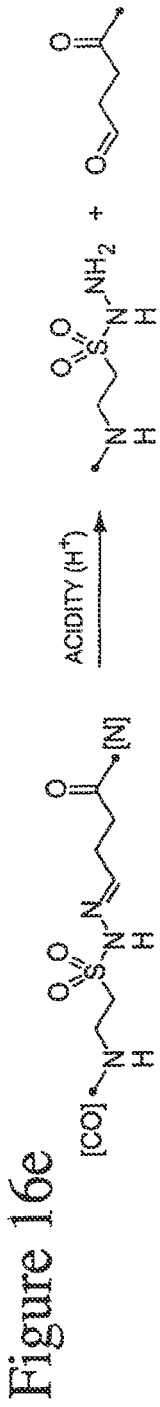
Figure 16F:
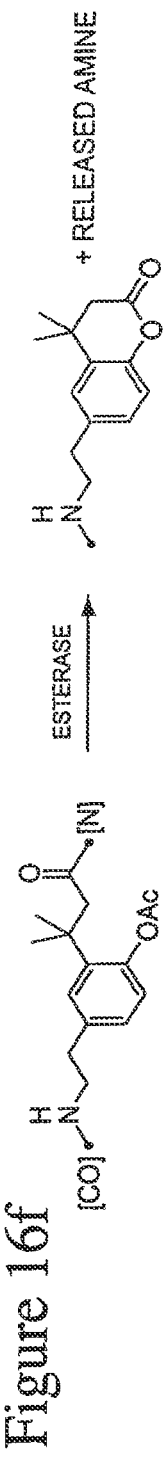
Figure 16G:
Figure 17A:
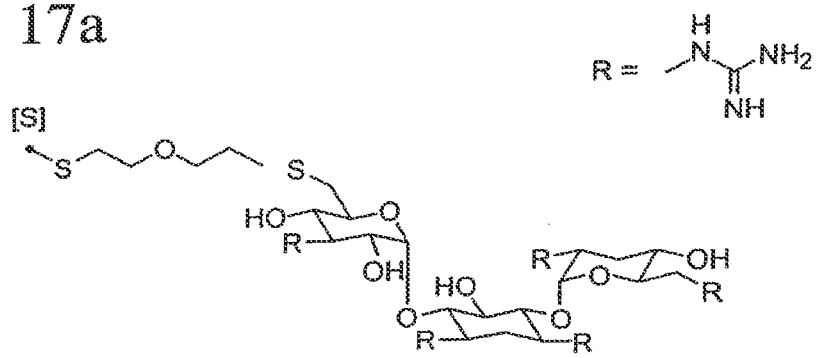
FIG. 17 illustrates some moieties suitable for use as part or all of a basic portion B.
FIG. 17e=SEQ ID NO:54.
FIG. 17f=SEQ ID NO:55.
Figure 17B:
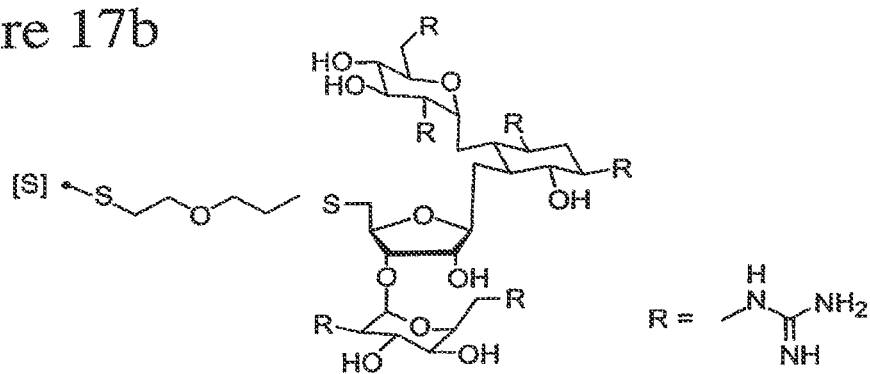
Figure 17C:
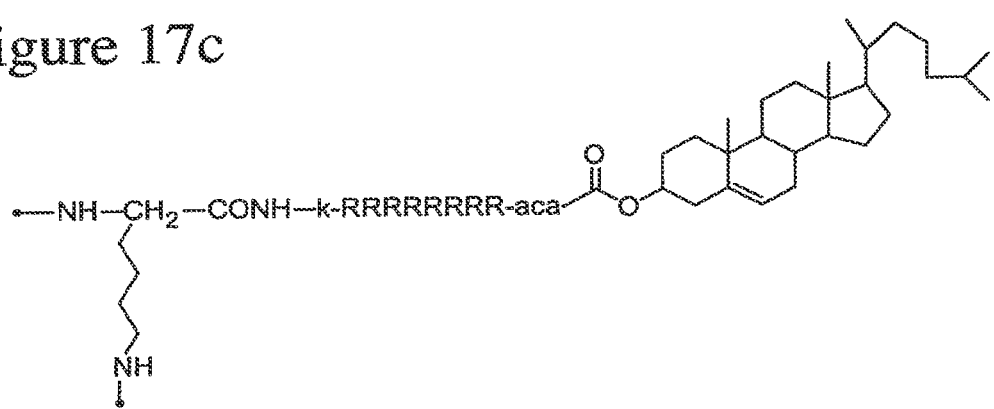
Figure 17D:
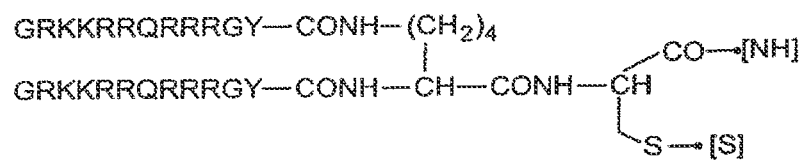
Figure 17E:
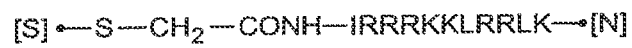
Figure 17F:
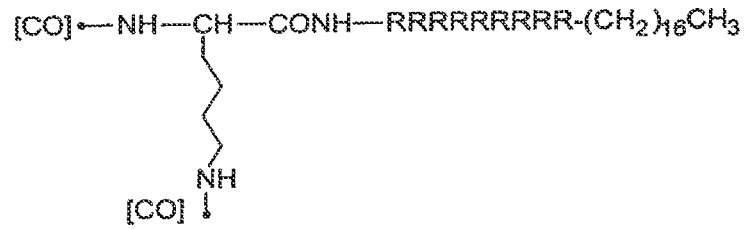
Figure 17G:
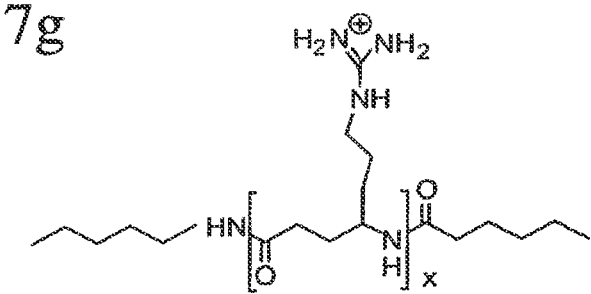
Figure 17H:
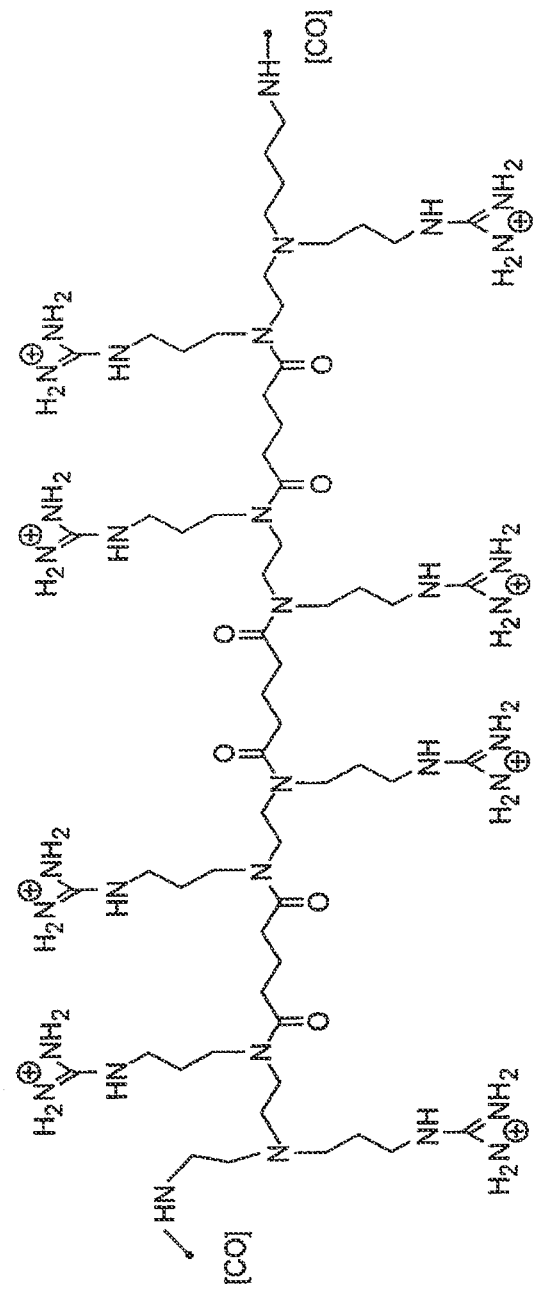
Figure 17I:
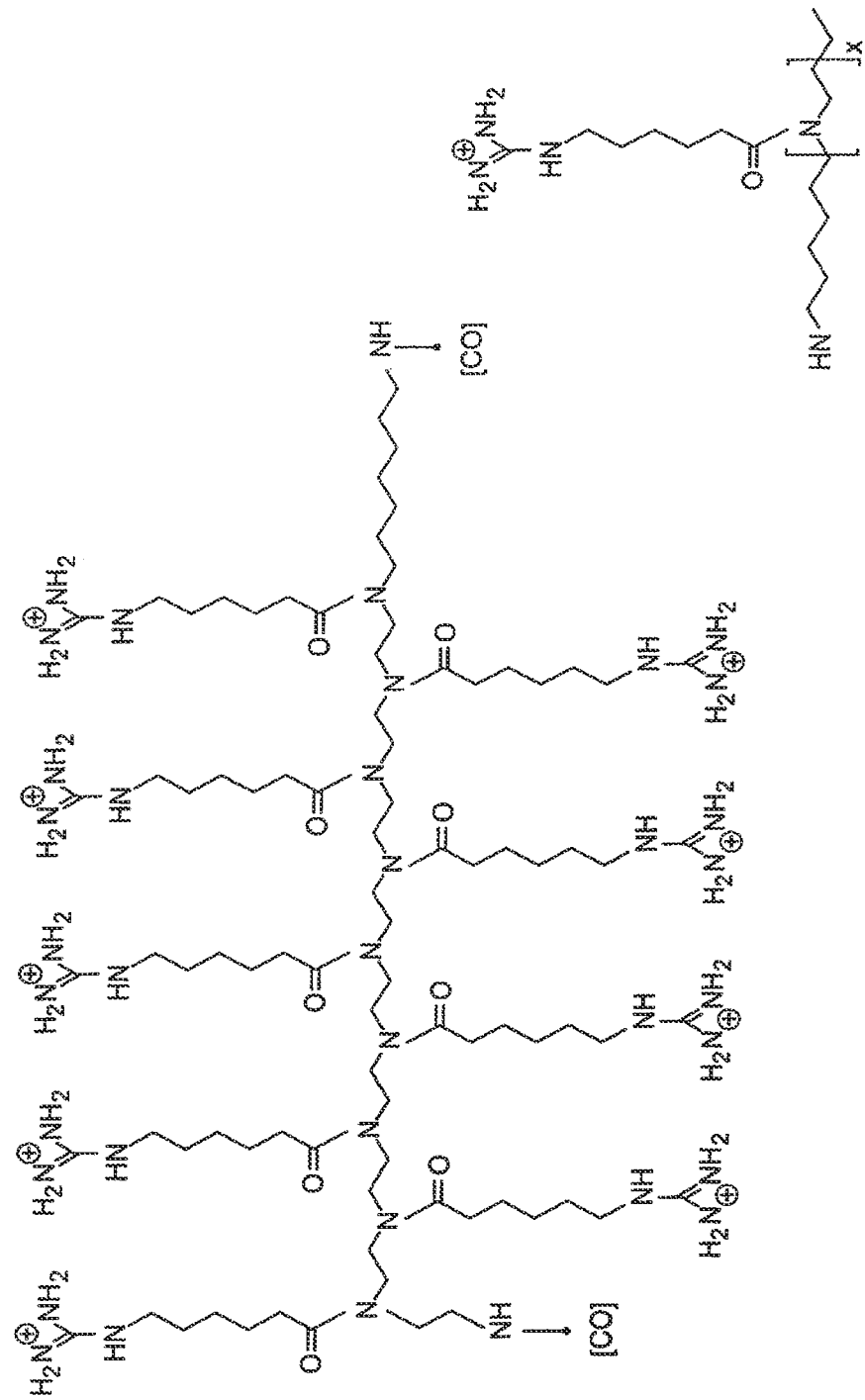
Figure 17J:
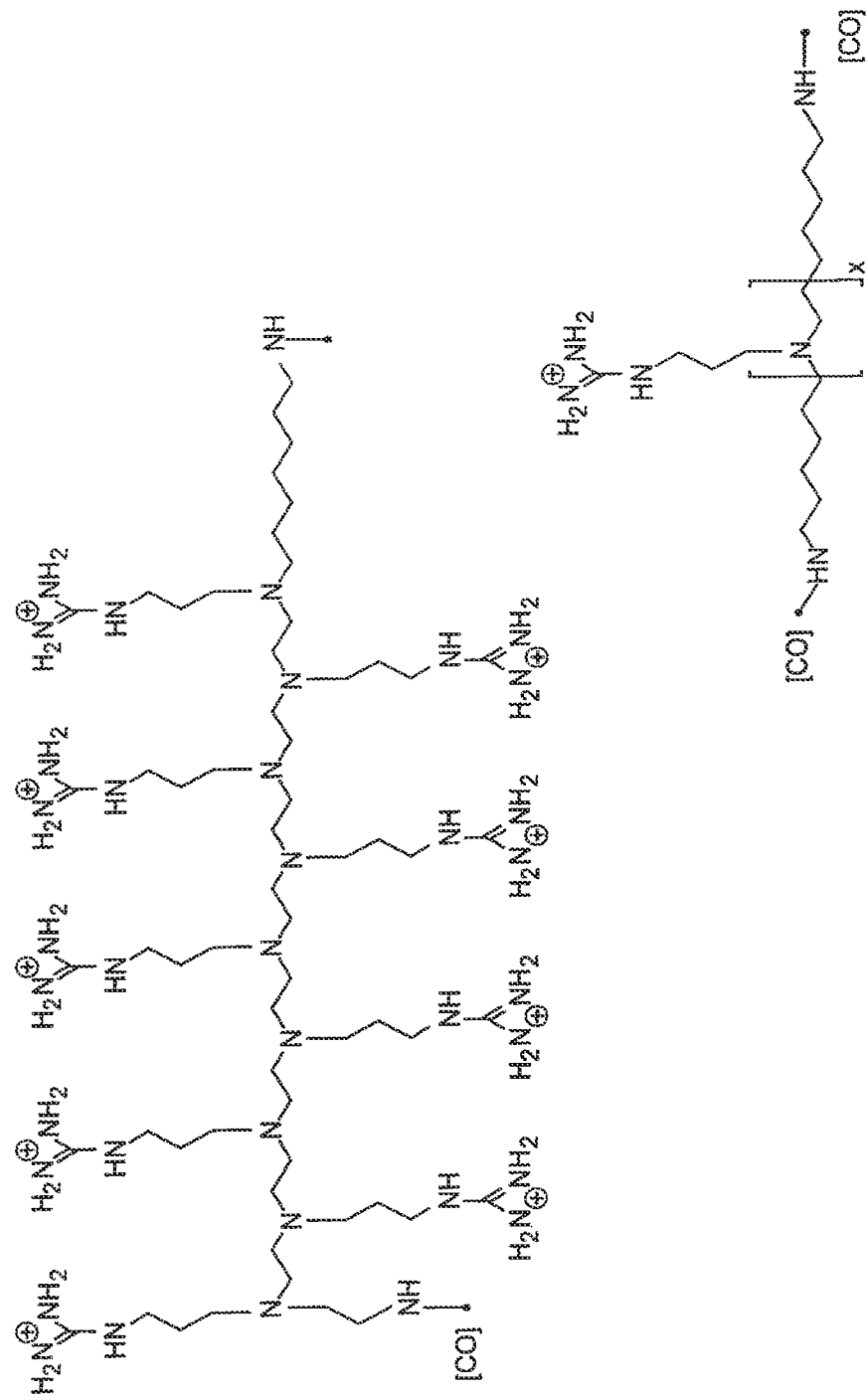
Figure 17K:
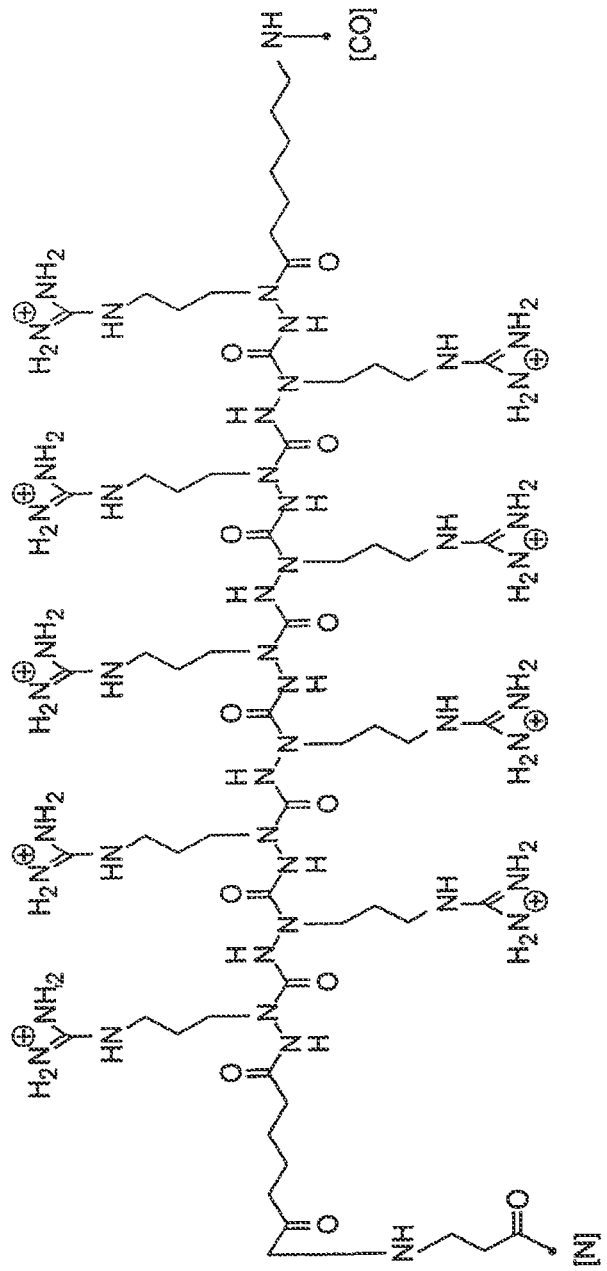
Figure 171:
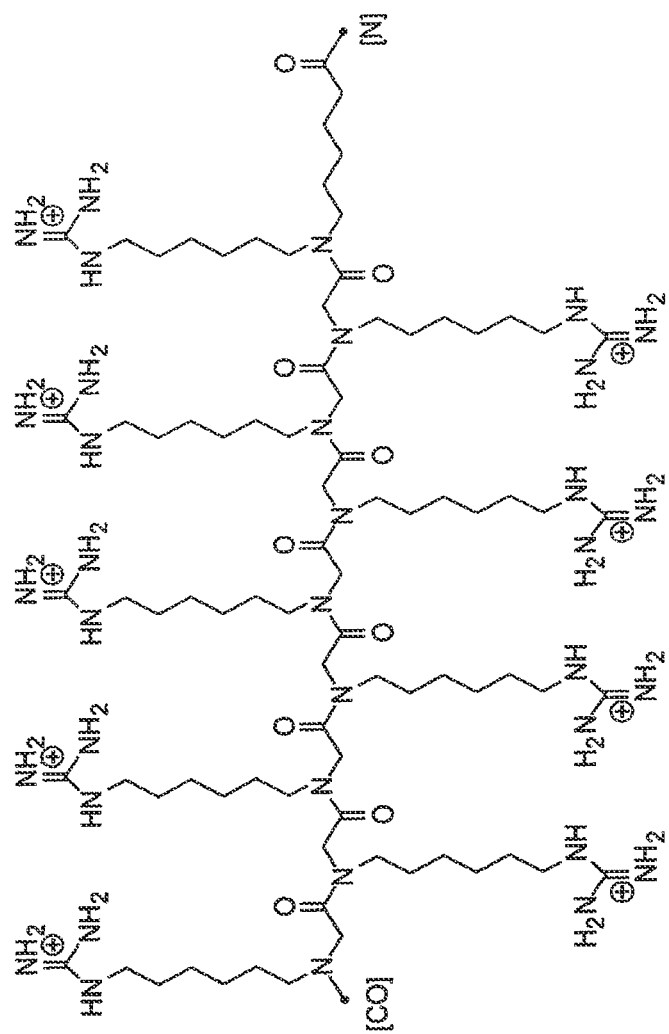
Figure 17M:
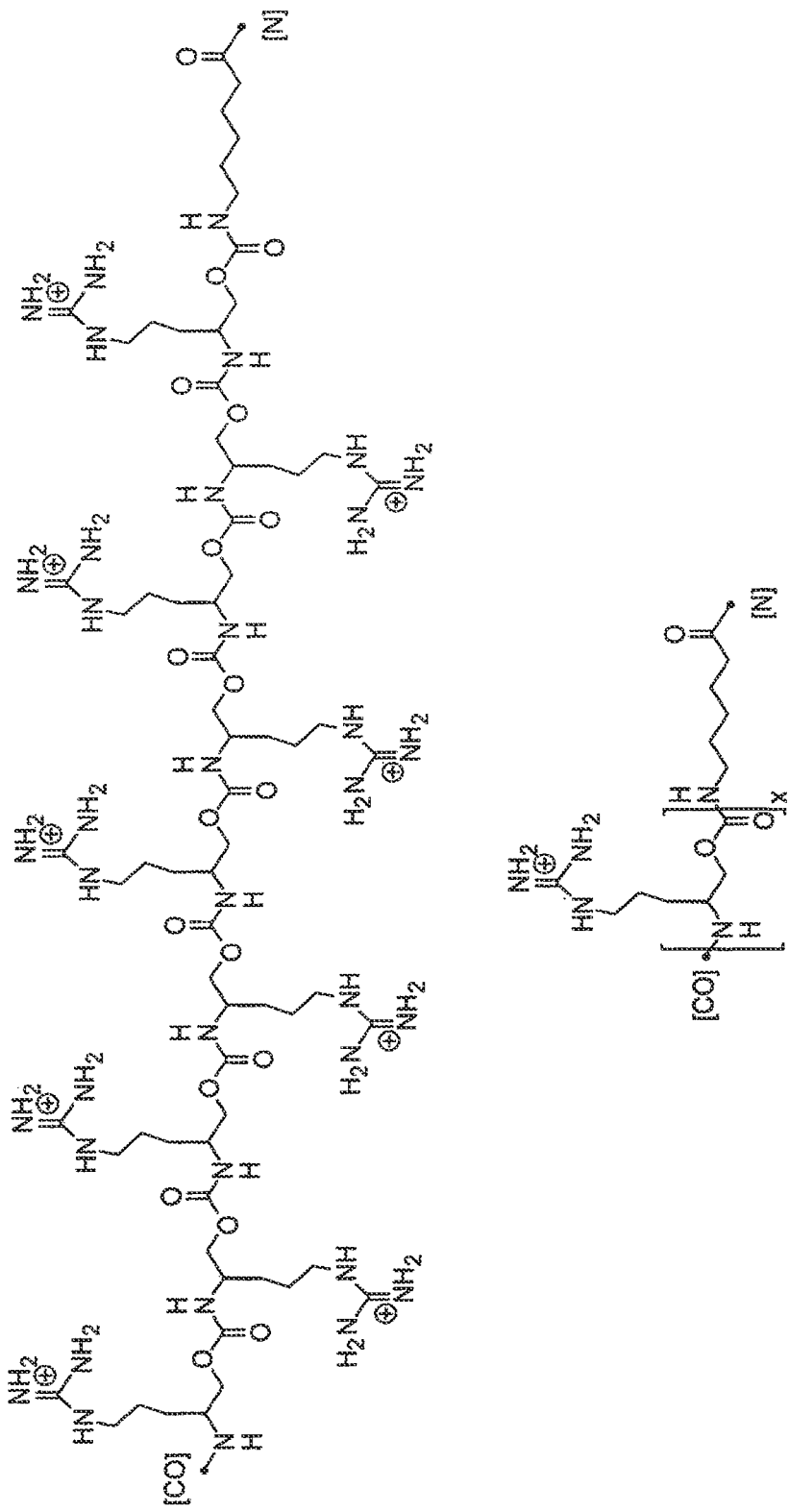
Figure 17N:
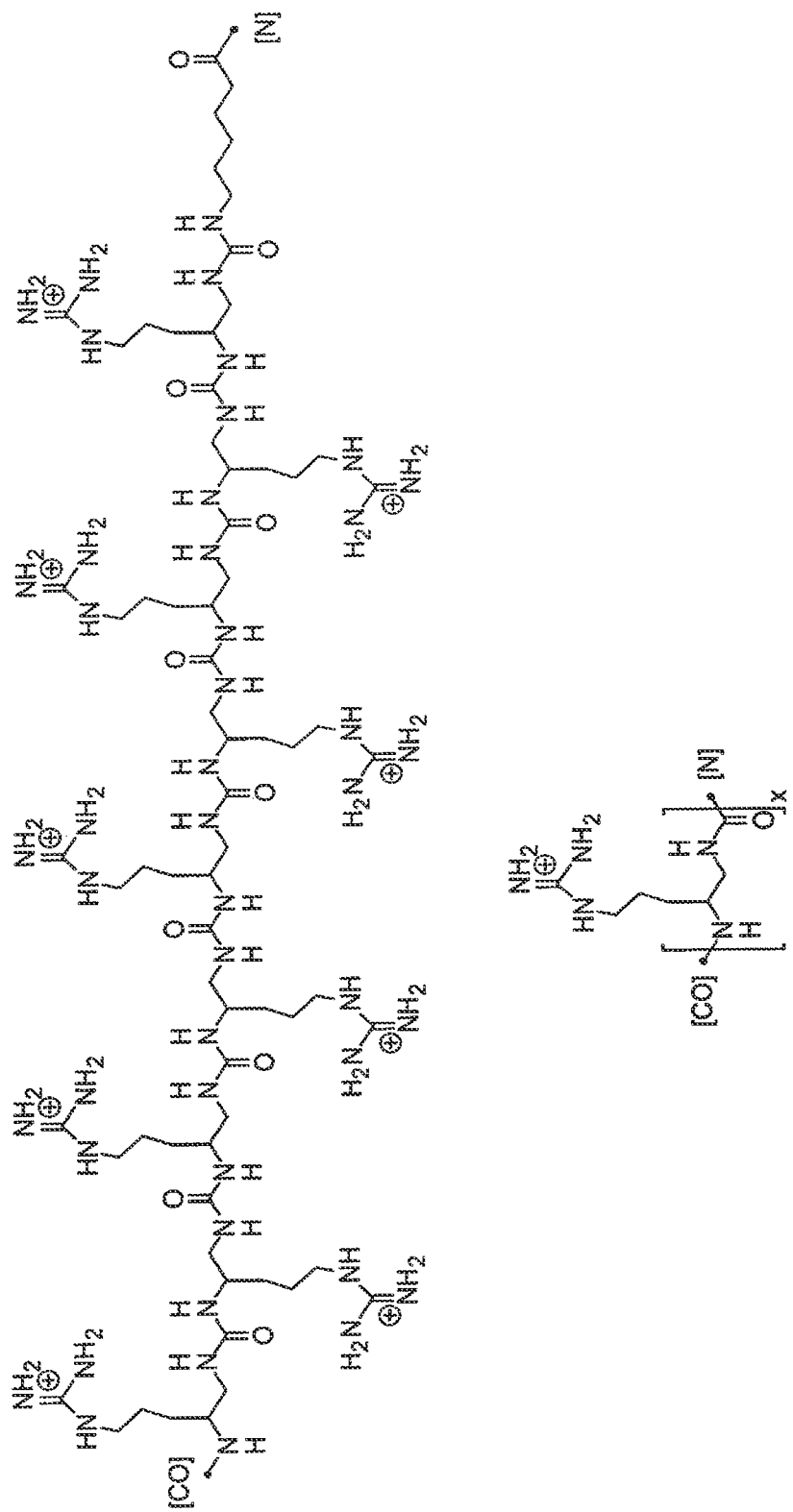
Figure 17O:
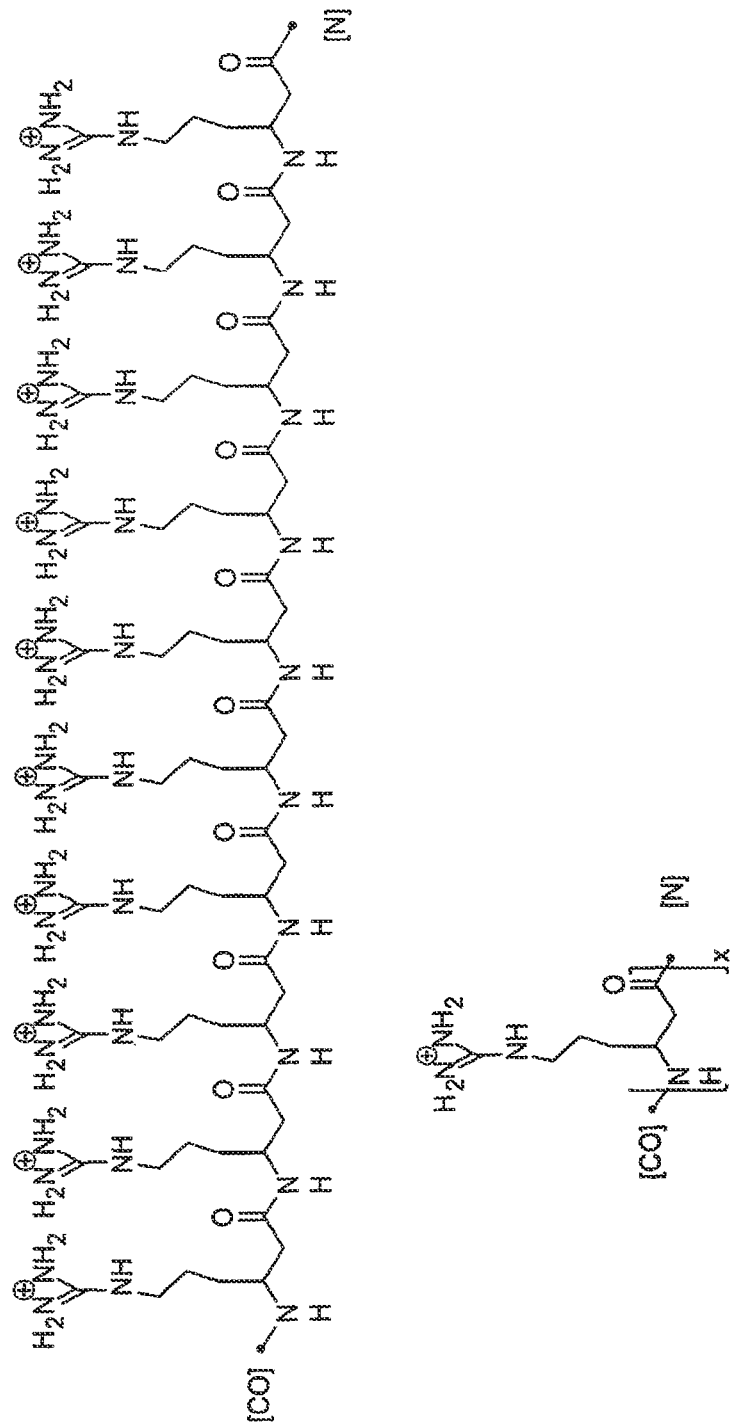

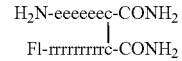

in which a disulfide bond between the two cysteines links the acidic portion H₂N-eeeeeec-CONH₂ with the basic portion Fl-rrrrrrrrrc-CONH₂. The basic portion carries the cargo portion, fluorescent moiety Fl (fluorescein). As illustrated in FIG. 13, the mean fluorescence measured in Jurkat cells incubated for ten minutes with the intact 7-45 peptide showed only a small amount of fluorescence above that of the background measured from the Jurkat cells alone. However, when the peptide was reduced with 25 mM tris(carboxyethyl)phosphine and 250 mM 2-mercaptoethanesulfonate for 15 min, which cleave the disulfide linker X, then incubated with Jurkat cells for ten minutes, the fluorescence taken up by the cells was comparable to that of cells incubated for 10 minutes in the presence of R10 (SEQ ID NO:49). Thus, a MTS molecule having features of the invention, with a disulfide linker X, is able to provide controlled delivery of cargo portion to cells.

Example 6

MTS Molecules Having Varying Lengths

MTS molecules having features of the invention may have different numbers of basic amino acids, different numbers of acidic amino acids, and different linkers. Several examples of different MTS molecules illustrating features of the invention are presented in this Example, in which a fluorescent cargo moiety is exemplified by fluorescein (Fl), a radioactive cargo moiety is exemplified by ¹²⁵I, and a therapeutic cargo by doxorubicin (DOX).

EDA-aca-R₅-aca-C(Fl)-CONH₂ (SEQ ID NO: 17)

EDDDDKA-aca-R₆-aca-C(DOX)-CONH₂ (SEQ ID NO: 18)

-continued

EEEDDDEEEDA-aca-R$_9$-aca-Y($^{125}$I)-CONH$_2$ (SEQ ID NO: 19)

ededdAAeeeDDDDKA-aca-R$_{11}$-aca-C(Fl)-CONH$_2$ eddedededDDDDKA-aca-R$_6$-AGA-R$_6$-aca-C(DOX)-CONH$_2$ Ggedgddeeeeeeddeed-aca-PLGLAG-aca-R$_8$-AAA-R$_{12}$-aca-C(Fl)-CONH$_2$ eeddeeddKA-aca-R$_7$-aca-C(Fl)-CONH$_2$ eDDDDKA-aca-RGRGRRR-aca-C(Fl)-CONH$_2$ eddddeeeeee-aca-PLGLAGKA-aca-R$_{10}$-aca-C(Fl)-CONH$_2$ eeeeeeeeeeeeeeee-aca-DDDDKA-aca-R$_{20}$-aca-C(Fl)-CONH$_2$ eeeeeeeeddddd-aca-DDDDKA-aca-R$_{17}$-aca-Y($^{125}$I)-CONH$_2$ ddddddddddddddddd-aca-PLGLAG-aca-R$_{14}$-aca-C(DOX)-CONH$_2$ Example 7

Examples of Molecules Suitable for Use as Cargo Moieties

Examples of molecules suitable for attachment as cargo moieties to a basic portion B of a MTS molecule having features of the invention are illustrated in FIG. 14. The different exemplary molecules shown in FIG. 14 are each labeled by an identifier letter in parentheses. The molecules are shown having one bond that ends in a dot; the bond ending in a dot may be used to attach the cargo molecule to a basic portion B. A letter in brackets near the dotted bond indicates a suitable atom to which the cargo molecule might bind; for example, [N] indicates that the cargo molecule may bind to a nitrogen, such as a nitrogen of a lysine epsilon amino group, or a nitrogen of an alpha amino group of a peptide backbone of the MTS molecule. An [S] indicates a linkage to a sulfur atom, such as a cysteine sulfur atom.

More than one of these exemplary cargo molecules may be attached to a basic portion B, and basic portions B carrying multiple cargo molecules may have more than one type of cargo molecule attached. The cargo molecules may form part of more complex structures as well. For example, the dark circle in the cargo moiety labeled (k) represents a particle including a superparamagnetic iron oxide core, jacketed by crosslinked, aminated dextran (such particles typically have a radius of about 22 nanometers). Although only one pendant group is shown, such particles may have multiple pendant groups (typically about 4 to about 20).

Example 8

Examples of Acidic Moieties Suitable for Inclusion in an Acidic Portion A

An acidic portion A may include acidic moieties such as those illustrated in FIG. 15. Such moieties may be linked to a linker X and an acidic portion A by peptide bonds, disulfide bonds, or other bonds. A dashed line in the illustration indicates a possible attachment point. In this and subsequent figures, a moiety in brackets indicates a Motif that may be repeated, with a letter (e.g., "x") indicating the number of times that the motif may be repeated (which may take on a number of possible values, typically between about 1 and about 100, preferably between about 1 and about 20). It will be understood that such acidic moieties may be attached to an acidic portion A in any suitable manner. In embodiments, an acidic portion A of a MTS molecule having features of the invention may be partly comprised of, or mainly comprised of, or essentially completely comprised of acidic moieties such as those illustrated in FIG. 15.

Example 9

Examples of Linker Moieties

Linkers suitable for use in a MTS molecule having features of the invention may be peptides or other molecules cleavable by enzymes under physiological conditions. For example, linkers may be cleavable by such enzymes as metalloproteases. Linkers cleavable by MMP-2 have been discussed supra, In addition, for example, linkers cleavable by other metalloproteases, such as MMP-9, MMP-1.1, and MMP-14 are also suitable. For example, peptide linker cleavable by MMP-9 may include the peptide sequence

PR(S/T)(L/I)(S/T) (SEQ ID NO: 29)

where the letters in parentheses indicate that either one of the indicated amino acids may be at that position in the sequence. A peptide linker cleavable by MMP-11 may include the peptide sequence

GGAANLVRGG (SEQ ID NO: 30)

and peptide linker cleavable by MMP-14 (MT1-MMP) may include the peptide sequence

SGRIGFLRTA. (SEQ ID NO: 31)

A peptide linker cleavable by urokinase plasminogen activator (uPA) may include the peptide sequence

SGRSA (SEQ ID NO: 32)

A peptide linker cleavable by lysosomal enzymes may include one of more of the peptide sequences

GFLG, (SEQ ID NO: 33)

ALAL, (SEQ ID NO: 34)
and

FK.

A peptide linker may be cleavable by a cathepsin. For example, a linker cleavable by cathepsin B may include a KK or a RR sequence, or may include both, where the cleavage would typically occur between the lysines or arginines. A peptide linker cleavable by cathepsin D may include the peptide sequence PIC(Et)F-F,  (SEQ ID NO: 35)

where C(Et) indicates S-ethylcysteine (a cysteine with an ethyl group attached to the thiol) and the "-" indicates the typical cleavage site in this and subsequent sequences. A peptide linker cleavable by cathepsin K may include the peptide sequence

GGPRGLPG.  (SEQ ID NO: 36)

A peptide linker cleavable by prostate-specific antigen may include the peptide sequence

HSSKLQ-.  (SEQ ID NO: 37)

A peptide linker cleavable by Herpes simplex virus protease may include the peptide sequence

LVLA-SSSFGY.  (SEQ ID NO: 38)

A peptide linker cleavable by HIV protease may include the peptide sequence

GVSQNY-PIVG.  (SEQ ID NO: 39)

A peptide linker cleavable by Cytomegalovirus protease may include the peptide sequence

GVVQA-SCRLA  (SEQ ID NO: 40)

A peptide linker cleavable by Thrombin may include the peptide sequence f(Pip)R-S where "f" indicates D-phenylalanine and "Pip" indicates piperidine-2-carboxylic acid (pipecolinic acid, a proline analog having a six-membered ring).

A peptide linker cleavable by Caspase-3 may include the peptide sequence

DEVD-.  (SEQ ID NO: 42)

A peptide linker cleavable by Interleukin 1β converting enzyme may include the peptide sequence

GWEHD-G.  (SEQ ID NO: 43)

In addition, linkers suitable for use in a MTS molecule having features of the invention may be cleavable by agents other than proteases under physiological conditions. Linkers may also be non-peptide molecules. Some examples of enzymatically and non-enzymatically cleavable moieties suitable as linkers are illustrated in FIG. 16. Examples of different cleavable linkers are shown along with an indication of conditions which lead to cleavage. For example, cleavage of the linker labeled (a) may be accomplished by beta-lactamase. Cleavage of the linker labeled (b) may be accomplished by exposure to light, such as to a single photon of violet light or to two photons of infrared light. Cleavage of the linker labeled (c) may occur under reducing conditions. Cleavage of the linkers labeled (d) and (e) may occur in acidic conditions. Action of an esterase may cleave the linker labeled (f), and a phosphatase may cleave the linker labeled (g).

Example 10

Examples of Basic Moieties Suitable for Inclusion in a Basic Portion B

A basic portion B may include basic moieties such as those illustrated in FIG. 17. Such moieties B may be linked to a linker X, cargo C, or to another part of a basic portion B by peptide bonds, disulfide bonds, or other bonds. A dot indicates a possible attachment point, while a letter enclosed by brackets indicates a possible atom to which such an attachment may be made (e.g., [S] indicates that a bond, such as a disulfide bond, may be made to a sulfur atom; a [N] indicates a bond to a nitrogen may be made). It will be understood that such basic moieties may be attached to a basic portion B or other portions of a MTS molecule in any suitable manner. For example, the "X" shown in compound (c) of FIG. 17 indicates attachment of a linker X to the side-chain of a D-lysine residue. The amino acid portion of compound (d) of FIG. 17 is SEQ ID NO: 45; the amino acid portion of compound (e) of FIG. 17 is SEQ ID NO: 46; and the amino acid portion of compound (I) of FIG. 17 is SEQ ID NO: 47. In embodiments, a basic portion B of a MTS molecule having features of the invention may be partly comprised of, or mainly comprised of, or essentially completely comprised of basic moieties such as those illustrated in FIG. 17.

It will be understood that some combinations of A and B may be more suitable than others. For example, it is preferred that the same backbone structure be present in both portions A and B in a MTS molecule having features of the invention, so that, for example, both A and B are peptides, or both A and B are peptoids, or both A and B are carbamates. It is also preferred that the absolute value of the net charge of one portion be similar, or the same as, the absolute value of the net charge of the other portion so that, for example, A has approximately the same number of negative charges as B has positive charges.

Example 11

Examples of Polymeric Acidic Portions

Figure 18A:
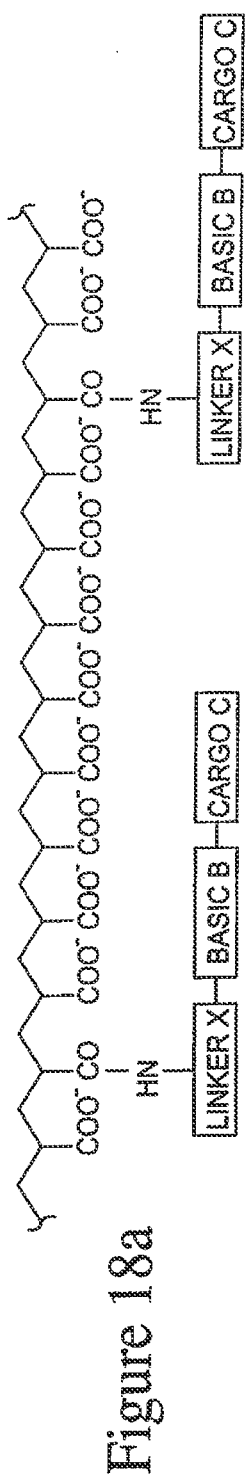
FIG. 18 illustrates some polymeric moieties suitable for use as part or all of an acidic portion A.
Figure 18B:
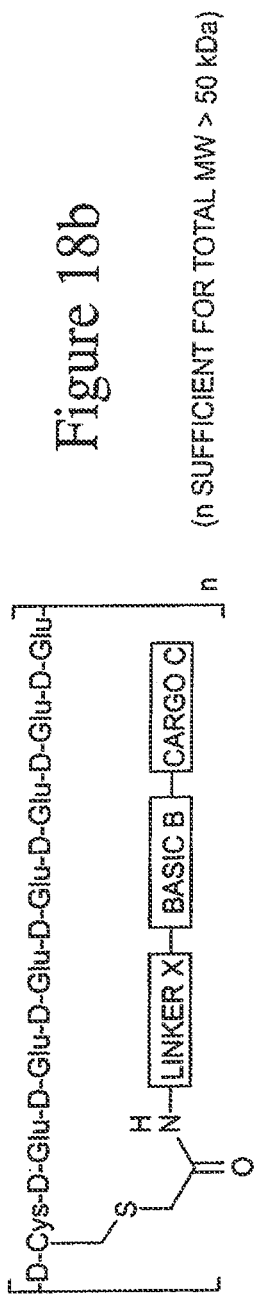
Figure 18C:
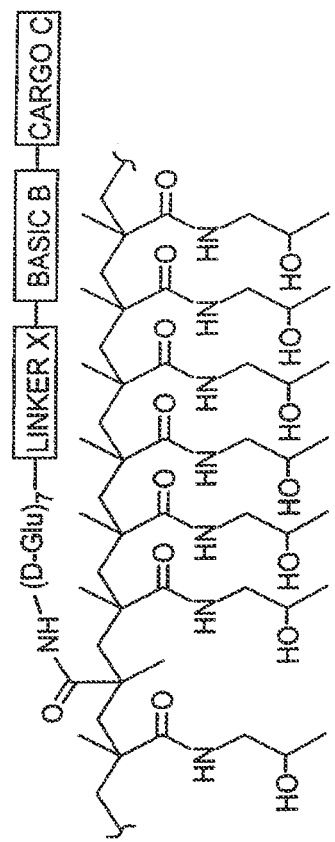

In another embodiment, an acidic portion A may include or be part of a polymer. In preferred embodiments, the polymer has an average molecular weight of about 50 kDa or above. Such high molecular weights reduce immunogenicity and improve pharmacodynamics by slowing excretion and lengthening the residence time in the bloodstream. Furthermore, polymers of such size benefit from "enhanced permeability and retention" (EPR) in tumors, whose capillaries are much leakier than normal tissue and whose lymphatic drainage is often impaired. These properties cause polymers to have higher ratios of concentrations in tumor vs. normal tissue than those of low-molecular-weight drugs. For recent discussions of the benefits of polymeric carriers, see Kopecek et al (2001) *J. Controlled Release* 74: 147-158; Luo & Prestwich (2002) *Current Cancer Drug Targets* 2: 209-226; Maeda et al (2003) *International Immunopharmacology* 3: 319-328; and Torchilin & Lukyanov (2003) *Drug Discovery Today* 8: 259-266. This EPR effect leading to enhancement of concentration in tumor tissue compared to normal tissue should further reinforce the tumor selectivity resulting from preferential cleavage of the linker X of MTS molecules having features of the invention by enzymes or under conditions found near tumors. Cleavage of X is effective to release basic portion B and cargo C attached to B from a polymeric acidic portion A, allowing the uptake of B and C into cells, In preferred embodiments, the polymer carries a sufficient number of negative charges to veto uptake of B and C while linker X is still intact. Examples of such polymers are shown in FIG. 18.

We claim:

1. A method for transporting a fluorescent moiety across a membrane of a cell, comprising:
contacting the cell with a molecule comprising Formula (I):

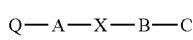    Formula (I)

wherein
C is a fluorescent cargo moiety,
B is a peptide with a sequence comprising a series of 5 to 20 basic amino acids,
A is a peptide with a sequence comprising 5 to 9 consecutive acidic amino acids, wherein the amino acids are selected from aspartates and glutamates,
X is a cleavable linker which is cleavable by a matrix metalloprotease, and
Q is a fluorescence-quenching moiety that quenches the fluorescence of C
whereby the cargo moiety is transported across the membrane of the cell following cleavage of the cleavable linker X.

2. The method of claim 1, wherein A is a peptide sequence comprising 8 consecutive glutamates.

3. The method of claim 1, wherein B is a peptide sequence comprising 9 to 16 consecutive arginines.

4. The method of claim 1, wherein B is a peptide sequence comprising 9 consecutive arginines.

5. The method of claim 1, wherein B is a peptide sequence comprising 8 consecutive arginines.

6. The method of claim 1, wherein (a) A is a peptide sequence comprising 8 to 9 consecutive glutamates arid (b) B is a peptide sequence comprising 9 consecutive arginines.

7. The method of claim 1, wherein X is cleaved in the extracellular space.

8. A method of labeling a cell, comprising:
contacting the cell with a molecule of Formula (I):

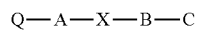    Formula (I)

wherein
C is a fluorescent cargo moiety,
B is a peptide with a sequence comprising a series of 5 to 20 basic amino acids,
A is a peptide with a sequence comprising 5 to 9 consecutive acidic amino acids, wherein the amino acids are selected from aspartates and glutamates,
X is a cleavable linker which is cleavable by a matrix metalloprotease, and
Q is a fluorescence-quenching moiety that quenches the fluorescence of C
whereby the marker cargo moiety is transported across the membrane of the cell following cleavage of the cleavable linker X.

9. The method of claim 8, wherein (a) A is a peptide sequence comprising 8 to 9 consecutive glutamates and (b) B is a peptide sequence comprising 9 consecutive arginines.

10. A method of labeling a cell in an individual in need thereof, comprising:
administering to an individual a molecule of Formula (I):

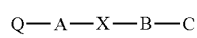    Formula (I)

wherein
C is a fluorescent marker cargo moiety,
B is a peptide with a sequence comprising a series of 5 to 20 basic amino acids,
A is a peptide with a sequence comprising 5 to 9 consecutive acidic amino acids, wherein the amino acids are selected from aspartates and glutamates, and
X is a cleavable linker which is cleavable by a matrix metalloprotease, and Q is a fluorescence-quenching moiety that quenches the fluorescence of C whereby the marker cargo moiety is transported across the membrane of the cell following cleavage of the cleavable linker X.

11. The method of claim 10, wherein (a) A is a peptide sequence comprising 8 to 9 consecutive glutamates and (b) B is a peptide sequence comprising 9 consecutive arginines.

\* \* \* \* \*